(12) United States Patent
Turgeon et al.

(10) Patent No.: US 11,051,535 B2
(45) Date of Patent: Jul. 6, 2021

(54) DEVELOPMENT OF AN ASPARAGINE-REDUCING YEAST BY ADAPTIVE EVOLUTION AND USES THEREOF TO REDUCE ACRYLAMIDE FORMATION

(71) Applicant: Renaissance BioScience Corp., Vancouver (CA)

(72) Inventors: Zachari J. Turgeon, Vancouver (CA); Jessica Marie Swanson, Vancouver (CA); Matthew S. Dahabieh, Vancouver (CA); John I. Husnik, Vancouver (CA)

(73) Assignee: Renaissance BioScience Corp., Vancouver (CA)

( * ) Notice: Subject to any disclaimer, the term of this patent is extended or adjusted under 35 U.S.C. 154(b) by 0 days.

(21) Appl. No.: 15/742,115

(22) PCT Filed: Jul. 6, 2016

(86) PCT No.: PCT/CA2016/050788
§ 371 (c)(1),
(2) Date: Jan. 5, 2018

(87) PCT Pub. No.: WO2017/004715
PCT Pub. Date: Jan. 12, 2017

(65) Prior Publication Data
US 2018/0192676 A1    Jul. 12, 2018

Related U.S. Application Data

(60) Provisional application No. 62/189,547, filed on Jul. 7, 2015.

(51) Int. Cl.
*A23L 5/20* (2016.01)
*A23L 19/18* (2016.01)
(Continued)

(52) U.S. Cl.
CPC ............... *A23L 5/28* (2016.08); *A21D 8/047* (2013.01); *A23F 5/02* (2013.01); *A23L 19/18* (2016.08);
(Continued)

(58) Field of Classification Search
None
See application file for complete search history.

(56) References Cited

U.S. PATENT DOCUMENTS 9,353,173 B2 *  5/2016  Chhun ................ C07K 14/705
2005/0239763 A1  10/2005  Motyka et al.
(Continued)

FOREIGN PATENT DOCUMENTS

SU    1742320 A1   6/1992
WO    98/31784 A1  7/1998
(Continued)

OTHER PUBLICATIONS

Dunlop, "L-Asparaginase of *Saccharomyces cerevisiae*: an extracellular Enzyme", J. Bacteriol., 1975, 122(3), pp. 1017-1024.*
(Continued)

*Primary Examiner* — Nghi V Nguyen
(74) *Attorney, Agent, or Firm* — Melanie Szweras; Bereskin & Parr LLP/S.E.N.C.R.L., s.r.l.

(57) ABSTRACT

The present disclosure relates to a method of isolating a yeast strain that is able to degrade L-asparagine under non-inducing conditions comprising repeated cycles of adaptive evolution and mutagenesis followed by strain selection. Also included are yeast strains obtained by the method, and methods and uses thereof for reducing asparagine, and thus acrylamide, during food preparation and processing.

8 Claims, 20 Drawing Sheets

Specification includes a Sequence Listing.

(51) Int. Cl.
  *A23L 33/14* (2016.01)
  *A21D 8/04* (2006.01)
  *A23F 5/02* (2006.01)
  *C12N 1/18* (2006.01)
  *C12N 9/82* (2006.01)
  *C12Q 1/34* (2006.01)
  *C12R 1/865* (2006.01)
  *C12Q 1/04* (2006.01)

(52) U.S. Cl.
  CPC .............. *A23L 19/19* (2016.08); *A23L 33/14* (2016.08); *C12N 1/18* (2013.01); *C12N 9/82* (2013.01); *C12Q 1/04* (2013.01); *C12Q 1/045* (2013.01); *C12Q 1/34* (2013.01); *C12R 1/865* (2013.01)

(56) References Cited

U.S. PATENT DOCUMENTS

| | | | |
|---|---|---|---|
| 2011/0052758 A1* | 3/2011 | Greiner-Stoeffele | C12N 9/82 426/45 |
| 2011/0086395 A1 | 4/2011 | Koopman et al. | |
| 2014/0335524 A1 | 11/2014 | Blondin et al. | |

FOREIGN PATENT DOCUMENTS

| | | |
|---|---|---|
| WO | 2008/128975 A1 | 10/2008 |
| WO | 2011106874 A1 | 9/2011 |

OTHER PUBLICATIONS

Kim (Asparaginase II of *Saccharomyces cerevisiae*, 1988—cited by the ISA and in the IDS filed on Jun. 26, 2018). (Year: 1988).*

John Q Kamerud et al.: "Asparaginase II of *Saccharomyces cerevisiae*: Selection of Four Mutations That Cause Derepressed Enzyme Synthesis", Journal of Bacteriology, vol. 165, Jan. 1, 1986, pp. 293-296.

L Kang et al: "Nitrogen catabolite repression in a glutamate auxotroph of *Saccharomyces cerevisiae*", Journal of Bacteriology, Jul. 1, 1982, pp. 29-35.

Kim, K. W., et al., Asparaginase II of *Saccharomyces cerevisiae*. Characterization of the ASP3 gene. Journal of Biological Chemistry, 263(24), 11948-11953, Aug. 25, 1988.

Dunlop, P. C., et al., Utilization of D-asparagine by *Saccharomyces cerevisiae*. Journal of Bacteriology, 125(3), 999-1004, Mar. 1976.

Roon, R. J., et al., Methylamine and ammonia transport in *Saccharomyces cerevisiae*. Journal of Bacteriology, 122(2), 502-509, May 1975.

Dragosits, M., et al., Adaptive laboratory evolution—principles and applications for biotechnology, Microbial Cell Factories, 12(1), 64, 2013.

Mondon, P. et al: "Comparative studies on the lethal, mutagenic, and recombinogenic effects of ultraviolet -A, -B, -C and visible light with and without 8-methoxypsoralen in *Saccharomyces cerevisiae*", Photochemistry and Photobiology, 1992., vol. 55, No. 5, pp. 713-721.

Roon et al: "Negative interactions between amino acid and methylamine/ammonia transport systems of *Saccharomyces cerevisiae*", The Journal of Biological Chemistry, 1977, vol. 252, No. 11, pp. 3599-3604.

English machine translation of SU1742320, published on Jun. 23, 1992.

Torres E.M. et al. Effects of Aneuploidy on Cellular Physiology and Cell Division in Haploid Yeast. Science, Aug. 17, 2007, vol. 317, Issue 5840, pp. 916-924. DOI: 10.1126/science.1142210.

* cited by examiner

■ Wild-type ■ RBAR-01 ■ RBAR-02 ■ RBAR-03

White bread - 0% sugar

White bread - 7% sugar

Whole wheat - 0% sugar

Whole wheat - 7% sugar

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Synthetic Primer

<400> SEQUENCE: 1
tcaacaatgg aatcccaac                                                    19

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2
catcttaaca ccgtatatga                                                   20

<210> SEQ ID NO 3
<211> LENGTH: 21
<212> TYPE: DNA
<213> ORGANISM: Artificial Sequence
<220> FEATURE:
<223> OTHER INFORMATION: Synthetic Primer

<400> SEQUENCE: 3
gagcggatga acagggatat t                                                 21

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
gggtctgtga ggttggaaat                                                   20

<210> SEQ ID NO 5
<211> LENGTH: 22
<212> TYPE: DNA
<213> ORGANISM: Artificial Sequence
<220> FEATURE:
<223> OTHER INFORMATION: Synthetic Primer

<400> SEQUENCE: 5
caaactgaga gtggacggta ag                                                22

<210> SEQ ID NO 6
<211> LENGTH: 21
<212> TYPE: DNA
<213> ORGANISM: Artificial Sequence
<220> FEATURE:
<223> OTHER INFORMATION: Synthetic Primer

<400> SEQUENCE: 6
gttgactata gctggcggaa a                                                 21

<210> SEQ ID NO 7
<211> LENGTH: 22
<212> TYPE: DNA
<213> ORGANISM: Artificial Sequence

```
<220> FEATURE:
<223> OTHER INFORMATION: Synthetic Primer

<400> SEQUENCE: 7
cgtctggatt ggtggttcta tc                                          22

<210> SEQ ID NO 8
<211> LENGTH: 22
<212> TYPE: DNA
<213> ORGANISM: Artificial Sequence
<220> FEATURE:
<223> OTHER INFORMATION: Synthetic Primer

<400> SEQUENCE: 8
ggaccacttt cgtcgtattc tt                                          22
```

DEVELOPMENT OF AN ASPARAGINE-REDUCING YEAST BY ADAPTIVE EVOLUTION AND USES THEREOF TO REDUCE ACRYLAMIDE FORMATION

CROSS-REFERENCE TO RELATED APPLICATIONS

This application is a national phase entry of PCT/CA2016/050788 filed Jul. 6, 2016 (which designates the U.S.), which claims the benefit of priority to U.S. Provisional Application No. 62/189,547 filed Jul. 7, 2015, the contents of which are incorporated herein by reference in their entirety.

INCORPORATION OF SEQUENCE LISTING

A computer readable form of the Sequence Listing "23756-P48552US01_SequenceListing.txt" (1,879 bytes), submitted via EFS-WEB and created on Jan. 4, 2017, is herein incorporated by reference.

FIELD

The disclosure relates to products and methods for reducing acrylamide concentration in food as well as to food products having a reduced acrylamide content. In particular, the disclosure relates to evolved yeast strains that have enhanced ability to reduce asparagine and thus acrylamide.

BACKGROUND

Acrylamide (AA) is an industrial chemical used to prepare polyacrylamide polymers used in waste water treatment, papermaking, ore processing, oil recovery, scientific research, and dye/fabric processing. Despite its widespread use, AA is highly toxic to biological systems, as evidenced by plethora of in vitro, in vivo, and animal model (rats and mice) studies (1-6). Taken together, these data firmly establish AA—and its active metabolite glycidamide—as toxic chemicals with potent mutagenic, cytotoxic, and neurotoxic potential.

As a result of its demonstrated toxicity in non-human systems, AA was classified by the World Health Organization's International Agency for Research on Cancer (WHO-IARC) in 1994 as a group 2A carcinogen-compounds in this group are listed as 'probably carcinogenic to humans' based on 'sufficient evidence of carcinogenicity in experimental animals and strong evidence that the carcinogenesis is mediated by a mechanism that also operates in humans'.

In 2002, AA was shown to occur in a variety of common human foodstuffs as a result of Maillard browning reactions that occur during cooking (7-9). More specifically, AA forms rapidly when the amino acid asparagine reacts with reducing sugars in starchy foods or food products once they are exposed to temperatures equal to or greater than 120° C. (e.g. frying, baking, roasting, etc.). Thus, AA is found in significant quantities in a wide variety of food products including bread (from all grain flours), potatoes, potato products (French fries, potato chips, potato flakes and flour), coffee, cereals, vegetables, etc. (10-19).

As a result of its ubiquity in food products, human dietary exposure to AA is widespread. However, there is currently no scientific consensus as to the direct role for dietary AA in causing human cancers. Although more than 30 epidemiological studies have been completed to date (20), many of these studies reach inconsistent or unclear conclusions, thus only supporting a correlative relationship between high dietary AA exposure and a variety of cancers, especially kidney, endometrial, and ovarian cancers (20).

Despite the lack of scientific consensus on the role of dietary AA in causing cancer, many of the world's governments and regulatory agencies have made the risk assessment and mitigation of dietary AA a significant priority. Indeed, the European Food Safety Authority (EFSA), WHO, U.S. Food and Drug Administration (FDA), California Office of Environmental Health Hazard Assessment (OEHHA) and Health Canada all consider the presence of AA in food to be a major concern and recommend reducing levels of AA in food and beverage to As Low As Reasonably Achievable (ALARA). Moreover, both the EFSA (Acrylamide Toolbox—http://www.fooddrinkeurope.eu/publications/category/toolkits/) and US FDA (http://www.fda.gov/Food/FoodborneIllnessContaminants/ChemicalContaminants/ucm2006782.htm) publish industry focused guidance documents for reducing AA in food and beverage.

Currently available methods for AA reduction are based on two basic principles: 1) mitigation of AA formation by food processing practices (limiting cooking time and temperature), and 2) elimination of asparagine as the AA precursor. Importantly, only the second strategy reduces the AA potential of foods, as AA can be formed during end-consumer cooking practices. In both commercially-produced and home-prepared foods alike, AA content increases significantly with cooking time and temperature (21). Thus, asparagine-removal based methods of AA reduction are considered superior as they eliminate the potential for downstream AA formation.

A number of methods are currently available for lowering the AA content of foods. These include preparations of the enzyme Asparaginase (Acrylaway®, Novozymes, Denmark and PreventASe, DSM, Netherlands)(http://www.acrylaway.com/en/Pages/default.aspx; http://www.dsm.com/markets/foodandbeverages/en_US/products/enzymes/baking/preventase.html), extensive yeast fermentation (22), applying glycine to dough prior to fermentation (23, 24), dipping potatoes into calcium chloride prior to frying (25), replacing reducing sugars with sucrose (26), general optimization of the processing conditions, such as temperature, pH and water content (25, 27, 28), studies regarding different choices of raw materials (27), and fermentation with lactic acid bacteria (Zerabac and Zeracid, Zeracryl, Norway; http://www.zeracryl.com/). Furthermore, a low asparagine breed of potato has been recently described (29-31), however this was created via recombinant DNA technology, and is thus considered a genetically modified organism (GMO) (http://www.simplotplantsciences.com/). All of these listed approaches are inadequate to some degree or have inherent issues that make them impractical during the manufacture of food products including cost, effect on organoleptic properties of the food, and/or ineffective acrylamide reduction under industrial scale food processing conditions.

Baker's yeast (*Saccharomyces cerevisiae*) is naturally capable of consuming/degrading the AA precursors, asparagine and reducing sugars. However, under most conditions common to food processing, the cellular machinery needed to degrade asparagine is turned off. Thus, unless used with very specific conditions and times, conventional yeast strains are ineffective at reducing AA. To circumvent this issue, the present inventors previously developed a novel, genetically modified (GMO), baker's yeast based technology to reduce acrylamide levels in food (US 2012/0321744

A1). This technology consisted of a specific strain of *S. cerevisiae*—engineered via recombinant DNA technology—for degrading asparagine and thus acrylamide. Although the yeast strain described in the US patent publication no. 2012/0321744 A1 is effective at reducing acrylamide in a wide variety of foods, the use of recombinant DNA technology in its development classifies the strain as a self-cloned, genetically modified organism (GMO). This designation inherently limits its adoption in industries and countries where GMO products are viewed negatively, and/or legislated against.

In *S. cerevisiae*, the genes responsible for asparagine degradation are ASP1 and ASP3, which encode an intracellular Asparaginase I and extracellular cell-wall associated Asparaginase II, respectively (32-34). ASP1 exists as a single copy gene (35), while ASP3 exists as a quadruple tandem repeat locus (36). Interestingly, the ASP3 locus is not native to *S. cerevisiae*, but was acquired through evolution by horizontal gene transfer from a non-*Saccharomyces* yeast species (*Wickerhamomyces*) (34).

It is well known that ASP1 is constitutively expressed, but is predominantly responsible for intracellular utilization of asparagine, rather than extracellular scavenging of asparagine for nitrogen (32, 33). As such, ASP1 activity alone is not sufficient for yeast to degrade significant amounts of asparagine for the purposes of reducing AA in food. To degrade extracellular asparagine, yeast must express Asparaginase II, however ASP3 is subject to mechanisms that selectively control nitrogen utilization in yeast, more commonly known as nitrogen catabolite repression (NCR) (37-41). In general, NCR refers to molecular mechanisms—consisting of sensing systems and transcriptional regulatory circuits—that permit differential gene expression of permeases and catabolic enzymes required to degrade nitrogen sources. More specifically, in cultures grown on multiple nitrogen sources, NCR permits yeast to sequentially catabolize different nitrogen sources, based on their relative biochemical utilization hierarchy (32, 42). In the context of ASP3, it is known that, like other NCR-regulated genes, the enzyme may be induced during growth in nitrogen-poor or deficient conditions—regardless of nitrogen source type—provided intracellular amino acid pools are depleted to a sub-threshold level (36, 37, 39, 40).

Random mutagenesis and adaptive evolution refers to the successive or iterative adaptation of an organism to novel growth conditions and/or environments. To accomplish this, random mutations are introduced in an organism, followed by characterization of large pool of variants, and selection of individuals with desirable traits. In this way, artificial selection is used to identify desirable genetic variability accelerated through mutagenesis (43). The technique is commonly used in microbiology to impart or enhance desirable traits in industrially relevant microbes and, more specifically, has a long history of use in the food industry (43-56). Importantly, adaptive evolution does not involve the use of recombinant DNA technology; therefore, organisms created by adaptive evolution are non-GMO (http://ec.europa.eu/food/plant/gmo/new/index_en.htm) and, as such, are not subject to restrictive GMO food legislation and customer acceptance issues.

By virtue of its nature, adaptive evolution always selects for the optimal way of accomplishing a task (52). Across large populations and over many generations, random mutation allows evolution to "try" every possible solution to a problem. Only those solutions which increase fitness—or at the very least are not overtly detrimental—will survive to the next generation (52). This concept becomes especially important when one considers that adaptations to a niche environment generally come at a fitness cost when outside of that environment (52). As such, adaptive evolution allows organisms to reach a fitness equilibrium with their environment. This equilibrium is made up of causative mutations for an adaptation of interest, as well as compensatory mutations that counteract generalized fitness loss as much as possible. In this way, adaptively evolved mechanisms can often be superior to targeted and specific methods such as recombinant DNA engineering.

Like other microorganisms, baker's yeast is highly amenable to random mutagenesis and adaptive evolution. Indeed, the technique has been used widely to modify traits relevant to industrial processes such as winemaking and bioethanol production (56). Adaptive evolution has also been used to study adaptation response to nitrogen-limiting environments (57, 58) and, more specifically, modify yeast's ability to use nitrogen (deregulation of NCR) for the treatment of wastewater (59). In addition, random mutagenesis and single-round selection has been used to isolate mutants of laboratory yeast with derepressed ASP3 in order to study mechanisms of NCR-mediated ASP3 regulation (60).

SUMMARY

The present inventors have demonstrated that by using a particular method of iterative adaptive evolution, a novel yeast strain having asparagine reduction activity under non-inducing conditions may be isolated.

Accordingly, the disclosure provides a method of isolating a yeast strain that degrades L-asparagine under non-inducing conditions comprising:

a) subculturing a wild-type yeast strain, which expresses or has the capacity to express a cell-wall associated Asparaginase, in the presence of media containing D-asparagine as the sole nitrogen source;

b) continuously subculturing, tracking growth rate and subjecting to mutagenesis weekly;

c) selecting cultures of b) when the growth rate reaches baseline;

d) continuously subculturing selected cells in selective media containing methylamine, tracking growth rate, and mutagenizing weekly until growth rate in the presence of methylamine reaches that in selective media without methylamine;

e) isolating individual colonies of d) by plating on selective media containing methylamine, growing said colonies and selecting large and fast growing colonies;

f) assaying selected colonies of e) for the ability to degrade L-asparagine under non-inducing conditions and selecting at least one colony with high L-asparagine degradation activity, as compared to cells at the start of d);

g) repeating steps d) through f) with the selected cells of f), increasing methylamine concentration each time, until L-asparagine degradation activity reaches a plateau;

h) isolating the strain from g) in which L-asparagine degradation activity has reached a plateau.

In one embodiment, the cell-wall associated Asparaginase is encoded by the ASP3 locus.

In one embodiment, the wild type yeast strain is an industrial yeast strain. In an embodiment, the yeast strain is an industrial baker's yeast strain.

Yeast strains may include, without limitation, genera and species from the kingdom Fungi. In one embodiment, genera and species may be selected from those used in food production. In another embodiment, the species are, without limitation, *Aspergillus acidus, Aspergillus niger, Aspergillus*

*oryzae, Aspergillus sojae, Candida etchellsii, Candida milleri, Candida oleophila, Candida rugosa, Candida tropicalis, Candida versatilis, Candida zemplinina, Candida zeylanoides, Cyberlindnera jadinii, Cyberlindnera mrakii, Cystofilobasidium infirmominiatum, Debaryomyces hansenii, Dekkera bruxellensis, Fusarium domesticum, Fusarium venenatum, Galactomyces candidum, Geotrichum candidum, Guehomyces pullulans, Hanseniaspora guilliermondii, Hanseniaspora osmophila, Hanseniaspora uvarum, Kazachstania exigua, Kazachstania unispora, Kluyveromyces lactis, Kluyveromyces marxianus, Lachancea fermentati, Lachancea thermotolerans, Lecanicillium lecanii, Metschnikowia pulcherrima, Mucor hiemalis, Mucor mucedo, Mucor plumbeus, Mucor racemosus, Neurospora sitophila, Penicillium camemberti, Penicillium caseifulvum, Penicillium chrysogenum, Penicillium commune, Penicillium nalgiovense, Penicillium roqueforti, Penicillium solitum, Pichia fermentans, Pichia kluyveri, Pichia kudriavzevii, Pichia membranifaciens, Pichia occidentalis, Pichia pijperi, Rhizopus microspores, Rhizopus oligosporus, Rhizopus oryzae, Rhizopus stolonifer, Saccharomyces bayanus, Saccharomyces cerevisiae, Schizosaccharomyces pombe, Schwanniomyces vanrijiae, Scopulariopsis flava, Starmerella bombicola, Torulaspora delbrueckii, Torulopsis candida, Torulopsis holmii, Trigonopsis cantarellii, Wickerhamomyces anomalus, Yarrowia lipolytica, Zygosaccharomyces rouxii, Zygotorulaspora florentina.* There are a variety of commercial sources for yeast strains, such as Lallemand Inc. (Canada), AB Mauri (Australia) and Lesaffre (France).

In one embodiment, the mutagenesis is physical mutagenesis, such as UV mutagenesis. In another embodiment, the mutagenesis is chemical mutagenesis.

In an embodiment, a) through c) occurs over 2-4 weeks. In an embodiment, d) through g) occurs over 6-48 weeks.

In one embodiment, the number of repetitions in g) is 5-20.

In another embodiment, the colonies are grown for 2-10 days in e) before selecting the large and fast growing colonies.

In one embodiment, in g) the amount of methylamine is increased gradually, for example, by 25-50% each repetition. In an embodiment, the amount of methylamine in e) is an amount sufficient to inhibit growth rate by 25-75% relative to growth rate in selective media without methylamine. In another embodiment, methylamine may be increased from 0.05 g/L to 12 g/L before L-asparagine degradation activity reaches a plateau.

Also provided herein is a yeast produced by a method disclosed herein. Even further provided is an isolated non-genetically modified yeast expressing a cell-wall Asparaginase and having asparagine reduction activity under non-inducing conditions. In one embodiment, the isolated non-genetically modified yeast reduces asparagine by at least 20%, at least 30%, at least 40%, at least 50% or more when grown under non-inducing conditions. In an embodiment, the cell-wall Asparaginase is constitutively expressed. In an embodiment, the cell-wall Asparaginase is encoded by the ASPS locus. In one embodiment, the yeast strain is an industrial yeast strain. In an embodiment, the yeast strain is an industrial baker's yeast strain.

Further provided is an isolated yeast strain deposited with the International Depositary Authority of Canada (IDAC) under accession numbers 140515-01 ("RBAR-01"), 140515-02 ("RBAR-02") and/or 140515-03 ("RBAR-03").

The present inventors have further shown that yeast strains disclosed herein are particularly useful for reducing asparagine, which thus reduces the formation of acrylamide during food preparation and processing. Accordingly, also provided herein is a method for reducing asparagine, and thus acrylamide formation during food preparation or processing, comprising adding a yeast strain as disclosed herein to food under food preparation or processing conditions; wherein the yeast reduces asparagine and thus acrylamide formation during the food preparation or processing.

In an embodiment, the yeast strain is inactive. In another embodiment, the yeast is fresh. In another embodiment, the yeast is active dry yeast.

The food product may be any food product that typically contains asparagine and, without limitation, includes a vegetable-based food product, a beverage, a bakery product, a grain product, a fruit, legume, dairy or meat product. In an embodiment, the food product is a bakery product, such as bread, biscuits, or pretzels. In one embodiment, the food product is a potato or potato-based product. In another embodiment, the food product is coffee.

In one embodiment, the food product is a potato or potato-based product and adding the yeast to food under food preparation or processing conditions comprises pre-soaking the potato or potato-based product in a mixture of water and the yeast strain prior to cooking.

In another embodiment, the food product is a potato-based snack food product and adding the yeast to food under food preparation or processing conditions comprises adding the yeast to a potato-based dough like system prior to forming, extruding, or otherwise creating a compressed product to be cooked by baking, frying, or roasting.

In another embodiment, the food product is coffee and adding the yeast strain to food preparation or processing conditions comprises soaking the fresh green coffee beans in green coffee bean extract that has been pre-treated with the yeast strain to reduce asparagine, such that the pre-treated extract depletes asparagine from the coffee beans prior to roasting.

In yet another embodiment, the food product is coffee and adding the yeast strain to food preparation or processing conditions comprises fermenting ground green coffee beans with the yeast strain prior to roasting.

Further provided herein is a food product having reduced asparagine produced using a yeast strain disclosed herein or a method disclosed herein.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

BRIEF DESCRIPTION OF THE DRAWINGS

The disclosure will now be described in relation to the drawings in which.

DETAILED DESCRIPTION

Figure 1:
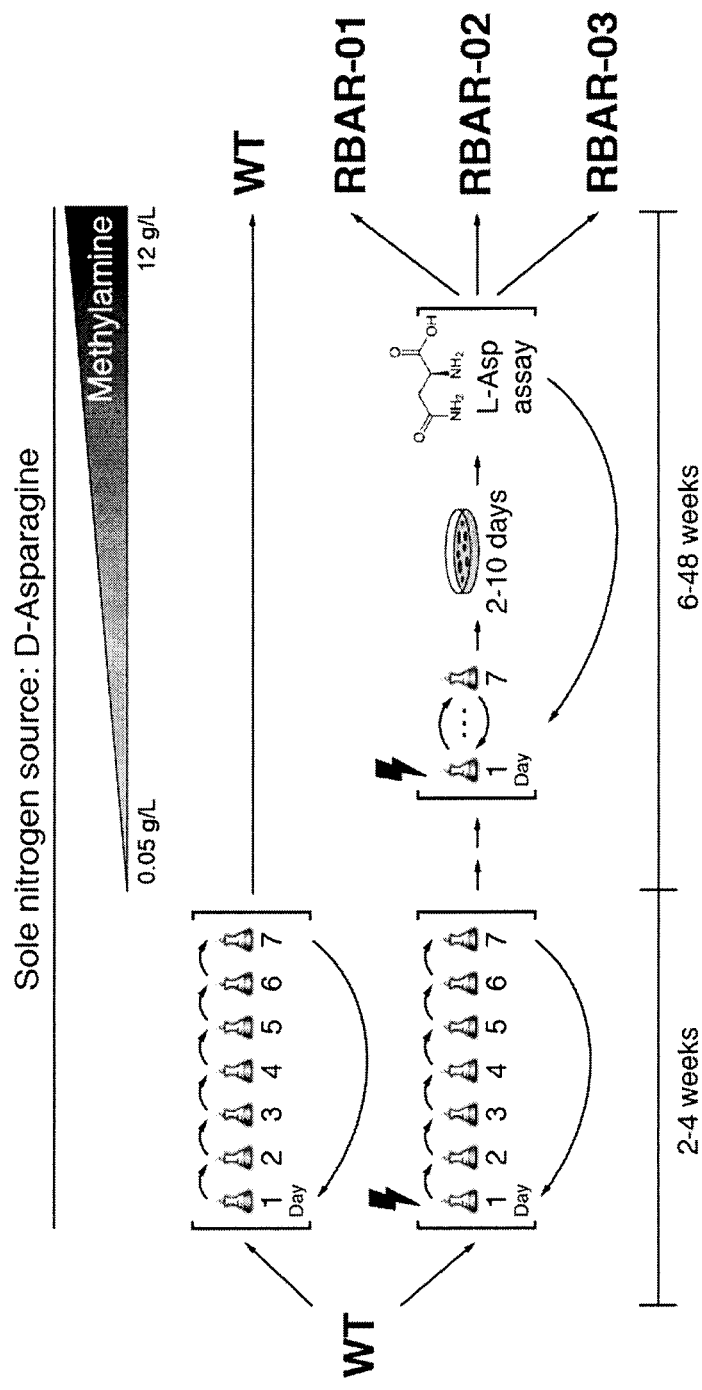
FIG. 1 is a schematic representation of the adaptive evolution strategy used to create the AR (acrylamide reducing) yeast strains disclosed herein.

The present inventors have demonstrated that an iterative process of random mutagenesis combined with selective pressure provided for the development of an industrial yeast strain having asparagine reduction activity under non-inducing conditions.

Accordingly, the disclosure provides a method of isolating a yeast strain that degrades L-asparagine under non-inducing conditions comprising:

a) subculturing a wild-type yeast strain, which expresses or has the capacity to express a cell-wall associated Asparaginase, in the presence of media containing D-asparagine as the sole nitrogen source;

b) continuously subculturing, tracking growth rate and subjecting to mutagenesis weekly;

c) selecting cultures of b) when the growth rate reaches baseline;

d) continuously subculturing selected cells in selective media containing methylamine, tracking growth rate, and mutagenizing weekly until growth rate in the presence of methylamine reaches that in selective media without methylamine;

e) isolating individual colonies of d) by plating on selective media containing methylamine, growing said colonies and selecting large and fast growing colonies;

f) assaying selected colonies of e) for the ability to degrade L-asparagine under non-inducing conditions and selecting at least one colony with high L-asparagine degradation activity, as compared to cells at the start of d);

g) repeating steps d) through f) with the selected cells from f), increasing methylamine concentration each time, until L-asparagine degradation activity reaches a plateau;

h) isolating the strain from g) in which L-asparagine degradation activity has reached a plateau.

In one embodiment, the cell-wall Asparaginase is encoded by the ASP3 locus (GenBank Accession Number NM_001182042.1).

In one embodiment, the wild type yeast strain is an industrial yeast strain. In an embodiment, the yeast strain is baker's yeast (*S. cerevisiae*).

The term "industrial yeast" as used herein refers to a strain used in industrial processes, contrasted with laboratory yeast which is typically used for research in the laboratory. Typically, industrial yeast tend to be predominantly diploid, with some being triploid, tetraploid, or aneuploid. Similarly, laboratory yeast tend to be haploid.

Yeast strains may include, without limitation, genera and species from the kingdom Fungi. In one embodiment, genera and species are selected from those used in food production. In another embodiment, the species are, without limitation, *Aspergillus acidus, Aspergillus niger, Aspergillus oryzae, Aspergillus sojae, Candida etchellsii, Candida milleri, Candida oleophila, Candida rugosa, Candida tropicalis, Candida versatilis, Candida zemplinina, Candida zeylanoides, Cyberlindnera jadinii, Cyberlindnera mrakii, Cystofilobasidium infirmominiatum, Debaryomyces hansenii, Dekkera bruxellensis, Fusarium domesticum, Fusarium venenatum, Galactomyces candidum, Geotrichum candidum, Guehomyces pullulans, Hanseniaspora guilliermondii, Hanseniaspora osmophila, Hanseniaspora uvarum, Kazachstania exigua, Kazachstania unispora, Kluyveromyces lactis, Kluyveromyces marxianus, Lachancea fermentati, Lachancea thermotolerans, Lecanicillium lecanii, Metschnikowia pulcherrima, Mucor hiemalis, Mucor mucedo, Mucor plumbeus, Mucor racemosus, Neurospora sitophila, Penicillium camemberti, Penicillium caseifulvum, Penicillium chrysogenum, Penicillium commune, Penicillium nalgiovense, Penicillium roqueforti, Penicillium solitum, Pichia fermentans, Pichia kluyveri, Pichia kudriavzevii, Pichia membranifaciens, Pichia occidentalis, Pichia pijperi, Rhizopus macrospores, Rhizopus oligosporus, Rhizopus oryzae, Rhizopus stolonifer, Saccharomyces bayanus, Saccharomyces cerevisiae, Schizosaccharomyces pombe, Schwanniomyces vanrijiae, Scopulariopsis flava, Starmerella bombicola, Torulaspora delbrueckii, Torulopsis candida, Torulopsis holmii, Trigonopsis cantarellii, Wickerhamomyces anomalus, Yarrowia lipolytica, Zygosaccharomyces rouxii, Zygotorulaspora florentina*. There are a variety of commercial sources for yeast strains, such as Lallemand Inc. (Canada), AB Mauri (Australia) and Lesaffre (France).

In one embodiment, the mutagenesis occurs by physical mutagenesis, including without limitation UV, and forms of radiation based mutagenesis such as X-ray and gamma ray mutagenesis. In an embodiment, the physical mutagenesis is UV mutagenesis. A person skilled in the art would readily know conditions for mutagenizing with UV. For UV mutagenesis, cells may be exposed to a UV light source (standard constant intensity) for varying amounts of time. Dosages may be based on kill rates—on average during each treatment cultures may be exposed to enough UV light to kill 25-90% of cells.

In another embodiment, the mutagenesis occurs by chemical mutagenesis (e.g. EMS—ethyl methanesulfonate).

Those skilled in the art would know that mutagenesis is used to increase the mutational rate and therefore the likelihood of finding mutations of interest under the proper selective conditions.

The term "non-inducing conditions" as used herein refers to any culture conditions under which extracellular L-asparagine degradation is normally repressed in wild-type yeast. In contrast, "selective conditions" refer to culture conditions where D-asparagine is the sole nitrogen source and for increased selective pressure, the presence of a growth inhibitor such as methylamine may be present.

A person skilled in the art would readily know conditions of culturing yeast cells. For example, for (a), yeast cells may be grown at 30° C. in liquid selective media, such as media composed of yeast nitrogen base without amino acids or ammonium sulfate (YNB-AA/AS) supplemented with a carbon source, such as 2% (w/v) sucrose, and D-asparagine, such as 10 g/L but the concentration may vary from 0.5 to 15 g/L depending on strains. Overnight cultures may be subcultured daily into fresh media at a consistent concentration, for example, to an optical density ($OD_{600}$) of 0.01.

For (d) selection with methylamine, cells may be grown at 30° C. in liquid selective media, such as media composed of yeast nitrogen base without amino acids or ammonium sulfate (YNB-AA/AS) supplemented with a carbon source, such as 2% (w/v) sucrose, and D-asparagine, such as 10 g/L but the concentration may vary from 0.5 to 15 g/L depending on strains, and further, supplemented with varying amounts of methylamine.

For (e) isolation of individual colonies selected with methylamine, cells may be plated and grown at 30° C. on solid selective media, such as media composed of yeast nitrogen base without amino acids or ammonium sulfate (YNB-AA/AS) supplemented with a carbon source, such as 2% (w/v) sucrose, D-asparagine, such as 10 g/L but the concentration may vary from 0.5 to 15 g/L depending on strains, and sufficient agar to solidify the media, and further supplemented with varying amounts of methylamine.

For general maintenance of yeast, cells may be grown at 30° C. on solid non-selective media, such as YEG agar media (2% yeast extract+1% glucose+2% agar).

Methods of determining growth rate are known in the art and examples of such measurements are described herein in the Examples. In one embodiment, the growth rate is determined by measuring optical density. Optical density is the fastest and most widely used method and relies on the fact that yeast in aqueous suspension scatter light. The amount of light scattered is proportional to the number of cells per unit volume i.e. cell concentration. In an alternate embodiment, growth rate is determined by counting the number of cells. The number of cells in a volume of culture can be counted precisely using a microscope and hemocytometer. In a further embodiment, growth rate on solid media can be determined by visually comparing colony size between cells grown in equivalent ways (i.e. same time, temperature, and media). For example, larger colonies will have grown faster than smaller colonies.

The phrase "large and fast growing colonies" as used herein refers to those colonies that have the fastest visual appearance and largest colony size relative to the approximate average size of colonies on the plate. Such identification can be qualitative in nature and a person skilled in the art would readily be able to determine those colonies that meet such criteria.

The term "baseline" in relation to growth rate as used herein refers to the growth rate of the strain on non-inducing and non-selective media (media containing good sources of nitrogen, i.e. nutrient rich media, i.e. not solely D-asparagine and/or containing methylamine).

In one embodiment, in g) the amount of methylamine is increased gradually, for example, by 25-50% each repetition such that initial increases are small and later increases are larger. In an embodiment, the amount of methylamine in e) is an amount sufficient to inhibit growth rate by 25-75% relative to growth rate in selective media without methylamine. In another embodiment, methylamine may be increased from 0.05 g/L to 12 g/L before L-asparagine degradation activity reaches a plateau.

Timeframes for subculturing and the total number of evolutionary iterations varies and depends on a number of variables including the genetic complexity of the wild-type strain, the type of mutagenesis used (i.e. chemical, UV, X-ray), the mutagenesis dose, and the strength of the selection. In an embodiment, the period of time for a) through c) is 2-4 weeks. In an embodiment, the period of time for d) through g) is 6-48 weeks. In an embodiment, the number of repetitions in g) is 5-20.

Colonies can be assayed for the ability to degrade L-asparagine under non-inducing conditions as described, for example, in the Examples section.

Also provided herein is a yeast produced by the methods disclosed herein. Even further provided is an isolated non-genetically modified yeast expressing a cell-wall Asparaginase and having asparagine reduction activity under non-inducing conditions. In one embodiment, the isolated non-genetically modified yeast reduces asparagine by at least 20%, at least 30%, at least 40%, at least 50% or more when grown under non-inducing conditions. A person skilled in the art can readily test the ability of a yeast strain to reduce asparagine using the methods disclosed in the Examples. In an embodiment, the cell-wall Asparaginase is encoded by the ASPS locus.

In an embodiment, the isolated non-genetically modified yeast constitutively expresses a cell-wall Asparaginase. Constitutive expression as used herein refers to continual gene expression throughout the growth of a microorganism, instead of selective expression depending on growth conditions. In one embodiment, the yeast strain is an industrial yeast strain. In an embodiment, the yeast strain is an industrial baker's yeast strain.

Further provided is an isolated yeast strain deposited on May 14, 2015 with the International Depositary Authority of Canada (IDAC) National Microbiology Laboratory, Public Health Agency of Canada, 1015 Arlington Street, Winnipeg, Manitoba, Canada R3E 3R2 under accession numbers 140515-01 (termed "RBAR-01" herein), 140515-02 (termed "RBAR-02" herein) and/or 140515-03 (termed "RBAR-03" herein). The deposit and viability receipts of these strains are found in Appendix A.

The present inventors have further shown that these evolved yeast strains are particularly useful for reducing asparagine, and in turn acrylamide during food preparation and processing and thus, the yeast strains disclosed herein are referred to as Acrylamide reducing yeast or AR Yeast. The terms "acrylamide reducing yeast" and "asparagine reducing yeast" are used herein interchangeably. Accordingly, also provided herein is a method for reducing asparagine, and in turn acrylamide during food preparation or processing, comprising adding a yeast strain as disclosed herein to food under food preparation or processing conditions; wherein the yeast reduces asparagine, and thus acrylamide formation during the food preparation or processing.

In an embodiment, the yeast strain is inactive. The term "inactive" as used herein refers to a composition of inactive, inviable and/or dead yeast organisms that still retain their nutritional content and other properties. For example, yeast may be grown under conditions that allow overexpression of the desired protein or proteins. The yeast can then be used to produce the inactive yeast, for example, through a variety of pasteurization methods including, without limitation, high-temperature and short-time pasteurization, a variety of sterilization methods including, without limitation, moist heat and irradiation, a variety of inactivation methods including, without limitation, high pressure, photocatalytic and pulsed-light, photosensitization, electric fields including RF and pulsed, cellular disruption, sonication, homogenization, autolysis, and chemical based inactivation including, without limitation, formaldehyde, thimerosol, chloramines, chlorine dioxide, iodine, silver, copper, antibiotics, and ozone.

In another embodiment, the yeast strain is fresh. In yet another embodiment, the yeast strain is active dry yeast. Fresh yeast refers to yeast which have been grown in non-selective yeast media (for example as defined above) and centrifuged to remove the majority of the liquid. Fresh yeast are live and metabolically active. Fresh yeast is not shelf stable and typically only lasts 1-5 weeks under refrigeration. Typical fresh yeast is approximately 25% solids. Active dry yeast (ADY) is a processed product in which yeast are dried to a final moisture content of 3% (97% solids). Yeast cells in this product are live but metabolically inert until rehydration. When vacuum sealed, ADY are typically shelf-stable for 2-4 years. Standardized procedures for making ADY are well known in yeast-based industries such as winemaking, brewing, and baking.

The phrase "reducing asparagine" as used herein refers to reducing the level of asparagine or degrading asparagine in for example a food product at least 20%, 30%, 40%, 50%, 60%, 70%, 80% or more compared to a control yeast strain, such as the parent strain from which the yeast strain was evolved.

Asparagine is a limiting precursor in the reaction that produces acrylamide during food preparation or processing. Accordingly, in another embodiment, there is provided a method for reducing acrylamide in a food product comprising adding a yeast strain as described herein to food under preparation or processing conditions; wherein the yeast reduces asparagine thereby reducing acrylamide in the food product. Also provided herein is use of the yeast strains disclosed herein for reducing acrylamide concentration during food preparation or processing conditions.

The phrase "reducing acrylamide" as used herein refers to reducing the level of acrylamide in the food product by at least 20%, 30%, 40%, 50%, 60%, 70%, 80% or more compared to in the absence of the yeast strain.

In one embodiment, the food preparation or processing conditions comprise fermentation. For example, the methods and uses herein are useful in fermenting of a food product, including without limitation, carbohydrate during breadmaking, potato processing, biscuit production, coffee production, or snack food manufacturing. The term "fermentation" as used herein refers to yeast consumption of sugars and other nutrients.

Accordingly, the food product may be any food product that typically contains asparagine and, without limitation, includes a vegetable-based food product, a beverage, a bakery product, a grain product, a fruit, legume, dairy or meat product. In one embodiment, the food product is a potato or potato-based product. In another embodiment, the food product is coffee.

In one embodiment, the food product is a potato or potato-based product and adding the yeast to food under food preparation or processing conditions comprises pre-soaking the potato or potato-based product in a mixture of water and the yeast strain prior to cooking. In an embodiment, the potatoes are pre-soaked at room temperature and air dried prior to cooking. The term "cooking" includes, without limitation, frying, roasting and baking. The concentration of the yeast strain disclosed herein in the water/yeast strain mixture, in an embodiment, is at least 1, at least 10, at least 50, at least 100 g/L (dry cell weight/volume), or more. The time of the pre-soak, in an embodiment, is at least 0.25 min, at least 0.5 min, at least 1 min, at least 5 min, at least 10 min, at least 20 min, or more.

In another embodiment, the food product is a potato-based snack food product and adding the yeast to food under food preparation or processing conditions comprises adding the yeast to a potato-based dough like system prior to forming, extruding, or otherwise creating a compressed product to be cooked by baking, frying, or roasting.

In another embodiment, the food product is coffee and adding the yeast strain to food preparation or processing conditions comprises soaking fresh green coffee beans in green coffee bean extract that has been pre-treated with the yeast strain disclosed herein to reduce asparagine, such that the pre-treated extract depletes asparagine from the coffee beans prior to roasting. In an embodiment, the extract is pre-treated at a temperature between 60° C. and 80° C., optionally at 70° C. The time of the extract pre-treatment, in an embodiment, is at least 1 hour, at least 5 hours, at least 10 hours, at least 15 hours, or more.

In yet another embodiment, the food product is coffee and adding the yeast strain to food preparation or processing conditions comprises fermenting ground green coffee beans with the yeast strain prior to roasting.

Further provided herein is a food product having reduced asparagine and, in turn reduced acrylamide, produced using a yeast strain disclosed herein or a method disclosed herein.

The food product can be any food product that is produced under preparation or processing conditions that result in the conversion of asparagine to acrylamide. Typical preparation and processing conditions that result in acrylamide formation include preparation involving high cooking temperatures (greater than 120° C.) and includes, without limitation, frying and baking, toasting, roasting, grilling, braising and broiling. Acrylamide is typically found in high concentration in potato products, bakery products and any cereal or grain product. Accordingly, in an embodiment, the food product is a vegetable, such as a potato, taro, or olive product, a bakery product or a cereal or grain product. Potato products include, without limitation, French fries, potato chips, fried/baked potato snacks and formed potato products. Bakery products include, without limitation, biscuits, cookies, crackers, breads, non-leavened bread products, battered products, corn and flour tortillas, pastries, pie crusts, cake and muffin mixes, and pastry dough. For example, breads can include, without limitation, fresh and frozen bread and doughs, sourdough, pizza dough, buns and rolls and variety breads, as well as related bread products such as fried or baked snacks or bread crumbs; and pastries can include, without limitation, sweet buns, donuts, and cakes. Cereal or grain products include, without limitation, typical breakfast cereals, beer malt and whey products, corn chips and pretzels, Other foods that are processed in high temperatures, include, without limitation, coffee, roasted nuts, roasted asparagus, beer, malt and whey drinks, chocolate powder, fish products, meat and poultry products, onion soup and dip mix, nut butter, coated peanuts, roasted soybeans, roasted sunflower seeds, fried or baked foods such as falafels and kobbeh, and chocolate bars.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Materials and Methods
Yeast Strains and Media

Yeast strains were maintained on YEG agar plates (2% w/v glucose, 1% w/v yeast extract, 2% w/v agar). Overnight cultures were grown from individual colonies inoculated into liquid YEG media and incubated for 18 hours at 30° C. (250 RPM).

Asparagine Breakdown Assay

The cell density of overnight cultures was measured by hemocytometer. Then $1 \times 10^7$ cells were inoculated into 5 mL of YEG media supplemented with 0.6 g/L L-asparagine and incubated at 30° C. At time points described in each experiment, 500 µL of media was removed, centrifuged at 13,000×g for 1 min (room temperature), and the supernatant transferred into a new tube. Asparaginase activity was inactivated by incubating the supernatant at 80° C. for 30 minutes. Residual L-asparagine in the supernatant was measured by enzymatic assay according to the manufacturer's instructions (Megazyme, K-ASNAM).

Intra-Delta Fingerprinting

Intra-delta fingerprinting was performed as described (61). Briefly, genomic DNA was extracted from overnight cultures using the phenol-chloroform method as previously described (62). Taq polymerase PCR reactions were assembled as follows: 100 ng genomic DNA, 1 µM of primer 1 (delta12: 5'-TCAACAATGGAATCCCAAC-3') (SEQ ID NO:1), 1 µM primer 2 (delta21: 5'-CATCT-TAACACCGTATATGA) (SEQ ID NO:2), 200 nM dNTP mix, 2.5 mM $MgCl_2$, 1× Taq buffer+KCl and 1 U Taq polymerase (Thermo Fisher, EP0402). Amplifications were performed on a BioRad C1000 thermocycler according to the following protocol: 4:00 at 95° C. (initial denature), 0:30 at 95° C., 0:30 at 46° C., 1:30 at 72° C. (35 cycles), 10:00 at 72° C. (final extension). PCR products were run on a 2% w/v HRB agarose gel (Amresco, E776) with standard TBE buffer at 8 V/cm, and imaged with GelGreen nucleic acid stain (Biotium).

RNA Extraction

5 $OD_{600}$ units of cells were isolated by centrifugation (13,000×g, 1 min, RT) and then snap frozen in dry ice/methanol. Total RNA was extracted using hot acidic phenol as previously described (63). Briefly, cells washed once with DEPC water and then lysed in TES buffer and acidic phenol-chloroform for 1 hour at 65° C. The liquid phase was purified with phase lock gel tubes (5Prime) and acidic phenol-chloroform followed by another phase lock gel tube and chloroform:isoamyl alcohol. RNA was ethanol precipitated over night at −80° C., washed with 70% ethanol, and resuspended in DEPC water.

Quantitative PCR (qPCR)

100 µg of raw total RNA was purified using an EZNA total RNA spin column (Omega Biotek) according to the manufacturer's instructions. Purified RNA was then quantified and checked for quality by RNA screen tape analysis (Agilent Technologies).

800 ng clean total RNA was converted to cDNA by reverse transcription according to the manufacturer's instructions (BioRad, iScript Reverse Transcription kit). Relative quantification of ASP1 and ASP3 expression was performed in triplicate. iTaq Universal SYBR Green qPCR reactions were assembled as follows: 8 ng cDNA, 500 nM of forward primer, 500 nM of reverse primer and 1× iTaq Universal SYBR Green Supermix (BioRad). Amplifications were performed on a StepOnePlus quantitative PCR thermocycler (Applied Biosystems) according to the following protocol: 0:30 at 95° C. (initial denature), 0:15 at 95° C., 1:00 at 60° C. (40 cycles), 65-95° C. in 0.5° C. increments (melt curve). Relative quantification data analysis was performed by the ΔΔCt method, normalizing to the housekeeping gene ACT1.

Primers for qPCR were as follows:

```
                                            (SEQ ID NO: 3)
ASP3_qPCR_Fwd  5'-GAGCGGATGAACAGGGATATT-3'

(SEQ ID NO: 4)
ASP3_qPCR_Rev  5'-GGGTCTGTGAGGTTGGAAAT-3'

(SEQ ID NO: 5)
ASP1_qPCR_Fwd  5'-CAAACTGAGAGTGGACGGTAAG-3'

(SEQ ID NO: 6)
ASP1_qPCR_Rev  5'-GTTGACTATAGCTGGCGGAAA-3'

(SEQ ID NO: 7)
ACT1_qPCR_Fwd  5'-CGTCTGGATTGGTGGTTCTATC-3'

(SEQ ID NO: 8)
ACT1_qPCR_Rev  5'-GGACCACTTTCGTCGTATTCTT-3'
```

DNA Sequencing

Genomic DNA was extracted from overnight cultures using the phenol-chloroform method as previously described (62). Nextera XT library preparation was performed according to the manufacturer's instructions (Illumine). Sequencing was performed on an Illumine MiSeq platform in a 2×300 bp paired-end configuration (GeneWiz).

RNA Sequencing

Total RNA was extracted, cleaned up, and quality controlled as described above. TruSeq v3 library preparation was performed according to the manufacturer's instructions (Illumine). Sequencing was performed on an Illumine HiSeq2500 High Output mode platform in a 2×100 bp paired-end configuration (GeneWiz).

Bread Production

Yeast for bread production was prepared by inoculating a loop of culture from a YEG plate into 75 mL liquid YEG medium. Cultures were grown for 18 hours (30° C.) and then scaled into 3×450 mL YEG media and grown for 24 hours as before. The yeast culture was harvested by centrifugation (10 min, 4,000×g, RT). Cream yeast were washed twice by re-suspension in sterilized water and centrifugation (10 min, 4,000×g, RT).

Yeast were activated by pre-fermenting for 45 minutes at 29° C. (Table 1), after which remaining ingredients were added to the pre-fermenting yeast and mixed for 21 min using a stand mixer (KitchenAid) fitted with dough hook (Table 2). The dough was incubated for 15 minutes at 22° C. ("floor time"), and formed into two equal loaves, and then incubated for 1.5 hours at 35° C. (or until the loaf doubles in size). The proofed loaves were then baked for 15 minutes at 204° C.

TABLE 1

Pre-fermentation mixture for bread making.

| Ingredient | % of flour (w/w) |
|---|---|
| Water | 25 |
| Yeast | 4.7 |
| Yeast extract | 0.5 |
| CaCO$_3$ | 0.1 |
| Sucrose sugar | 1 |
| Salt (NaCl) | 0.5 |

TABLE 2

Final ingredient mixtures for bread making.

| Ingredient | White Bread | Whole Wheat |
|---|---|---|
| Yeast cake | 4.67 | 4.67 |
| Water (38 °C.) | 58.33 | 58.33 |
| White flour | 100 | 50 |
| Whole wheat flour | — | 50 |
| Sucrose sugar | 0, 7 | 0, 7 |
| Vegetable oil | 4 | 4 |
| Salt (NaCl) | 2.17 | 2.17 |

*Amounts listed as % of flour (w/w)

Following baking, bread loaves were cooled to RT and cut into 1.4 cm slices. Bread samples were toasted using a standard kitchen toaster fitted with a digital thermometer (VWR Traceable). Toasting levels were defined by toaster temperature as follows: light—167° C.; medium—217° C.; high—235° C. Bread and toast samples were then milled (IKA analytical mill Model A11BS1) and homogenized.

French Fry Production

Yeast for French fry production was prepared as previously described for bread.

Russet potatoes were peeled, rinsed, chopped and blanched in 90° C. water for 10 min in order to deactivate browning enzymes. The blanched potatoes were drained, cooled to RT, and added to either water alone, or a mixture of AR yeast and water (Table 3). Potatoes were incubated in the water/yeast mixture at RT, and samples were taken at 10, 20, 40 and 60 min, after which the samples were immediately air-dried at 80° C. for 10 min. Dried potato samples were then cooked in corn oil at 175° C. (Table 3).

For testing the efficacy of the AR yeast under short processing times and high temperatures, 50 g of potatoes were incubated for 50 seconds in either 100 mL of water alone, or 100 mL water with either 100, 200, 250, or 300 g/L of AR yeast cream yeast (23% solids) at 68° C. Prior to potato addition, the yeast/water mixtures were equilibrated to 68° C. for 10 minutes. After treatment, samples were immediately air-dried at 80° C. for 10 minutes. Dried potato samples were then cooked in corn oil in a batch fryer at 175° C. for 5 minutes. French fries and AR yeast treatments were performed in triplicate. Statistical significance was determined by the Student's T test, relative to the 0 g/L AR yeast control.

TABLE 3

Yeast mixtures and cooking parameters for potato processing.

| | g/L of water | | Cook temp | Cook time | Thickness |
|---|---|---|---|---|---|
| | Potato | Yeast | (° C.) | (min) | (mm) |
| French fries | 200 | 100 | 175 | 5 | 10 × 10 |

Snack Pellet Production

Yeast for snack pellet production was prepared as previously described above for bread.

Snack crumb ingredients were added to a stand mixer (KitchenAid) fitted with flat paddle attachment and mixed for 5 min according to (Table 4). The crumb was extruded into pellets (approximately 2 cm long) using a 4 mm diameter die. The resultant pellets were dried in a single layer at 60° C. for 3-3.5 hours to a target moisture content of 11%. Pellets were stored for 1 week in an airtight plastic bag then deep-fried for 10 sec at 185° C.

TABLE 4

Final ingredient mixture for snack pellet production

| | % of total ingredient weight |
|---|---|
| Potato granules | 51.05 |
| Potato flakes | 6.63 |
| Potato starch | 6.63 |
| Salt | 1.66 |
| Maltodextrin | 0.33 |
| Water (target 38% moisture) | 29.52 |
| Yeast (approx. 25% solids) | 4.23 |

Sweet Biscuit Production

Yeast for biscuit production was prepared as previously described for bread.

Sweet biscuit ingredients (Table 5) were processed by blending oil, syrup and sugar for 1 min at high speed using flat paddle attachment (KitchenAid Classic Stand Mixer). The leavening agent and/or yeast was dissolved into the ingredient water and added to the mixing bowl. The dry ingredients were added and mixed for an additional 6 min. The resultant dough was rested for 20 min. 13 g of biscuit dough were pressed into a 65 mm diameter circular mold and baked at 180° C. for 6 min (target moisture: 2.5-3.5%).

TABLE 5

Final ingredient mixture for sweet biscuit production

| | % of total weight |
|---|---|
| Oil | 16.6 |
| Sucrose Sugar | 16.9 |
| Corn Syrup | 6 |
| Salt | 0.50 |
| Baking soda/Yeast (DWB) | 0.90 |
| All purpose flour | 19.20 |
| Rolled oat flour | 38.00 |
| Water | 1.90 |

Pretzel Production

Yeast for pretzel trial was prepared as previously described for bread.

Pretzels were prepared by first mixing dry ingredients (Table 6), water and yeast for 1 min using stand mixer (Kitchen Aid classic stand mixer) fitted with flat paddle attachment. The shortening was added and dough was mixed for an additional 5 min and then fermented for 30 min at 35° C. The fermented dough was extruded through 9 mm die approx. 40 mm in length then rested for 10 min. The pellets were cooked for 20 sec at 94° C. in an alkaline bath (1% NaOH). Pretzels were then baked for 25 min at 204° C. (target moisture 15%). The baked product was dried at 119° C. for 25 min (target moisture 3.5%).

TABLE 6

Final ingredient mix for pretzel production

| | % of Ingredient wt. |
|---|---|
| Wheat Flour | 64.5 |
| Yeast | 0.5 |
| Leavening Agent | 0.5 |
| Shortening | 2.00 |
| Salt | 1.00 |
| Sucrose | 2.00 |
| Water | 29.50 |

Coffee Production

Yeast for coffee trial was prepared as previously described for bread.

Direct Coffee Bean Fermentation

Green coffee beans (GCB) (Brazil Serra Negra) were ground into a powder (IKA analytical mill Model A11 BS1). Reverse osmosis water was added at a rate of 75 mL per 40 g GCB powder. 4 g of Cream yeast (25% solids) or 3 g RO water for the no yeast control was added to the GCB paste and fermented for 20 hr in a shaking incubator (250 rpm 30° C.). 10 g of fermented paste was roasted in IR moisture meter (Ohaus MB45-2A0) for 13 minutes at 200° C.

Green Coffee Extract Preparation and AR Yeast Treatment

Green coffee extracts (GCE) were prepared by iteratively soaking batches of GCB in water. More specifically, 500 g GCB were soaked in water for 16 hours at 70° C. and then discarded. Then, fresh GCBs were pre-soaked in water for 1 hour at 70° C. before incubating in the GCE for 16 hours at 70° C. This process of soaking fresh GCBs in the GCE was repeated until the soluble solids content reached 18%.

GCE was treated with AR yeast by incubating various concentrations of the AR yeast with GCE at room temperature for various times. After treatment, AR yeast-treated GCE was clarified by centrifugation and used for asparagine measurement.

Acrylamide Quantitation by UPLC-QDA

Serving size portions of solid foods were pulverized in a food processor prior to sampling. Liquid and powdered food products were sampled directly. Samples of 1.00 g were weighed into 50 mL centrifuge tubes, and 1 mL of 200 µg/kg $^{13}C_3$-labeled acrylamide internal standard and 9 mL water were added. Each tube was then capped and shaken by hand or vortexed briefly to mix the contents of the tube. The tubes were clamped in a rotating shaker to mix the tube contents for 20 min. The tubes were centrifuged at 9000 rpm for 15 min with an Eppendorf 5810R centrifuge. A 5 mL aliquot of clarified aqueous layer was promptly removed by pipet for spin filtration. The pipet was inserted through the top oil layer, avoiding the bottom solids layer with the pipet tip when a portion of the aqueous phase was removed. The 5 mL aliquot was placed in a spin filtration tube and centrifuged at 9000 rpm for 2-4 min. If the filter clogged, a new filter tube was inserted, the unfiltered liquid was poured onto the new filter, and centrifugation was continued until most of the liquid had passed through the filter. Oasis HLB SPE cartridges were conditioned with 3.5 mL of methanol followed by 3.5 mL of water; the methanol and water portions were discarded. Each cartridge was loaded with 1.5 mL of filtered extract. The extract was allowed to pass through the sorbent material followed by 0.5 mL of water. Then the column was eluted with 1.5 mL of water, and the eluant was collected for Accucat SPE cleanup. The outside of the Accucat SPE cartridges was marked at the height of 1 mL of liquid above the sorbent bed, and then the A cartridges were conditioned with 2.5 mL of methanol followed by 2.5 mL of water. The methanol and water portions were discarded. All of the eluant collected from the Oasis SPE was loaded and eluted to the 1 mL mark before the remainder of the eluted portions was collected. These portions were transferred into 2 mL amber glass autosampler vials for Liquid Chromatography/Mass Spectrometry (LC-MS) analysis on a Waters ACQUITY UPLC H-Class coupled with Waters ACQUITY QDa mass detector using the following settings:

Mobile phase composition: Aqueous 0.1% formic acid, 2% methanol

Column: Waters ACQUITY UPLC HSS T3 2.1×50 mm 1.8 µm

Column flow rate: 500 µL/min

Column temperature: 20° C.

Injection volume: 5 µl

Elution time: 1 minute

Ionization mode: Positive ion electrospray

Capillary voltage: 600 V

Cone voltage: 5 V

MS mode: SIR monitoring m/z 72.04

L-Asparagine Quantitation in Coffee Bean Extract by UPLC-PDA

Coffee bean extract was centrifuged at 13,000 rpm for 5 minutes at room temperature. The resulting supernatant was diluted with Milli-Q water for measuring L-asparagine by Waters Ultra Performance Liquid Chromatography (UPLC) system equipped with a Photodiode Array (PDA) detector (Acquity UPLC H-Class, Waters, Milford, Mass., USA) and an Acquity UPLC BEH C18 column (1.7 µm, 2.1 mm×100 mm, Waters, Milford, Mass., USA). L-asparagine of 99.6% purity (Sigma-Aldrich, St. Louis, Mo., USA) was obtained to prepare standard solutions with a concentration range from 15 to 500 pmole/µL for calibration and calculation. L-asparagine in both samples and standard solutions was derivatized by AccQ•Tag Ultra™ Derivatization Kit (WATERS, Milford, Mass., USA) to add a chromophore group for detection of its absorbance at 260 nm. The analysis was carried out with an injection volume of 1 µL and column temperature at 43° C. AccQ•Tag Ultra™ Eluent A and Eluent B concentrate solutions were purchased from Waters (Milford, Mass., USA) for gradient elution of the L-asparagine derivative. The detailed elution program was shown as follows in Table 7:

TABLE 7

Elution Program:

| Time (min) | Flowrate (mL/min) | % A | % B | % C | % D |
|---|---|---|---|---|---|
| Initial | 0.7 | 10.0 | 0.0 | 90.0 | 0.0 |
| 0.29 | 0.7 | 9.9 | 0.0 | 90.1 | 0.0 |
| 5.49 | 0.7 | 9.0 | 80.0 | 11.0 | 0.0 |
| 7.10 | 0.7 | 8.0 | 15.6 | 57.9 | 18.5 |
| 7.30 | 0.7 | 8.0 | 15.6 | 57.9 | 18.5 |
| 7.69 | 0.7 | 7.8 | 0.0 | 70.9 | 21.3 |
| 7.99 | 0.7 | 4.0 | 0.0 | 36.3 | 59.7 |

TABLE 7-continued

Elution Program:

| Time (min) | Flowrate (mL/min) | % A | % B | % C | % D |
|---|---|---|---|---|---|
| 8.59 | 0.7 | 4.0 | 0.0 | 36.3 | 59.7 |
| 8.68 | 0.7 | 10.0 | 0.0 | 90.0 | 0.0 |
| 10.20 | 0.7 | 10.0 | 0.0 | 90.0 | 0.0 |

Solvent A: Eluent A concentrate
Solvent B: 10% Eluent B in water
Solvent C: Water
Solvent D: Eluent B concentrate Results Evaluation of an Existing Single-Round Screening Method for ASP3 Derepression Mutants In order to circumvent the NCR that normally keeps ASP3 repressed, a random mutagenesis-screening method that selects for yeast cells able to grow on D-Asparagine as the sole nitrogen source was used (60). Like all other known life, Saccharomyces cerevisiae does not utilize D-amino acids. However, the cell wall-associated Asparaginase II (ASP3) enzyme is unique in that it can degrade D-asparagine, albeit inefficiently (64). Importantly, the cytosolic Asparaginase I (ASP1) cannot degrade D-asparagine.

While growth on D-asparagine indicates that ASP3 is being produced, it must also be expressed in strong NCR conditions in order to be fully derepressed. Thus, the selection method also incorporated methylamine in the media. S. cerevisiae cannot utilize methylamine as a nitrogen source. However, methylamine competes with ammonium ions for ammonia transporters. Once in the cell, methylamine does not participate in metabolic reactions, but does cause strong NCR—equivalent to growth on yeast's preferred nitrogen source: ammonia (ammonium sulfate). Thus, methylamine is a growth inhibitor (65, 66).

Culturing cells in media containing D-asparagine as the sole nitrogen source and methylamine sets up conditions in which the only way the cells can grow is to express ASP3, degrade external D-asparagine, and then import the released ammonium ions. Simultaneously, the liberated ammonium ions must compete with methylamine in order to be used for growth by the cell. Thus, the cells with the greatest expression levels of ASP3 gain a selective advantage due to the repressing conditions of the growth media. Importantly, the yeast cannot use the released D-aspartic acid for growth.

This selection method (D-asparagine and methylamine) was previously used to identify derepressed ASP3 mutants in a laboratory strain of yeast (DJ2-23C) (60). The authors selected for the ASP3 mutants by directly plating the EMS mutagenized cells onto selective plates (with 100 mM (3.1 g/L) methylamine and 5 mM (0.66 g/L) D-asparagine). This led the authors to find a variety of derepressed ASP3 variants. However, after repeated efforts it was not possible to replicate those results in a relevant industrial baker's yeast strain.

It is important to note that the authors of the original study (Kamerud and Roon 1986) were likely able to easily find derepressed ASP3 mutants because they were using haploid laboratory yeast strains. Using an industrial strain—with a significantly more complex genome (triploid, tetraploid, aneuploid) —makes finding derepressed mutants substantially more difficult. This is because any mutations with a recessive phenotype will not be displayed, as they would be in a haploid strain. There is also significantly more opportunity for epistasis or pleiotropic mutations to occur. Essentially, any single beneficial mutation will be buffered by genetic redundancies. This is rare in a laboratory strain, especially those with a haploid background.

Development of a Random Mutagenesis and Adaptive Evolution Strategy to Obtain an Acrylamide-Reducing Yeast Given that industrial baker's yeast are not amenable to the single round selection strategy of Kamerud and Roon, the screening method was redesigned to incorporate an iterative adaptive evolution strategy in combination with multiple rounds of mutagenesis (FIG. 1). The goal of this novel strategy was to slowly increase selective pressure over time, in conjunction with repeated mutagenesis, so as to allow for full ASP3 expression—and therefore asparagine breakdown—in otherwise repressive conditions. Importantly, the selective conditions necessary to ensure full derepression of ASP3 had to be increased slowly, as the final concentrations of D-asparagine and methylamine used for selection completely prevent the growth of non-adapted yeast. Thus, only the specific combination of random mutagenesis and adaptive evolution employed was capable of yielding the AR phenotype.

A culture collection of commercially available, industrial yeast strains was screened for growth on D-asparagine as the sole nitrogen source. Only one industrial strain—a Japanese baker's yeast strain—had any appreciable growth on D-asparagine, indicating it contained native ASP3 genes. The laboratory strain S288C was used as a positive control, as it is known to contain ASP3.

At time zero, the wild-type strain was first subcultured in minimal media contain D-asparagine (10 g/L) as the sole nitrogen source (sucrose as the carbon source). In this media, the wild-type exhibited a very slow growth rate, and under these conditions, cells with natural mutations allowing for slightly higher expression of ASP3 have a selective advantage. In order to introduce genetic variability, cells were subjected to UV mutagenesis on a weekly basis, at varying doses of UV (10-99% lethal dose). The strain was continuously sub-cultured (on a daily basis) and $OD_{600}$ readings were taken to track relative growth. Upon each sub-culture, cells were inoculated into fresh media at the same starting $OD_{600}$ of 0.01. Over a period of four weeks, the growth rate of the mutagenized yeast on selective media was observed to increase, such that it was comparable to the growth rate on non-selective media. This suggested that the inventors had selected for cells with increased expression of ASP3 under non-inducing conditions, thus giving a good genetic background to start to select for derepressed mutants (in conditions of strong NCR or non-inducing conditions) with maximal expressive potential.

After one month, methylamine was introduced to the culture media in order to drive strong NCR i.e. fully repressive conditions for ASP3. Using the mutagenized lineage as a starting point, a minimal amount of methylamine was added to the growth media (0.05 g/L). This significantly reduced the growth rate of the cells to the same rate as when sub-culturing on the selective media first began.

Over the next four months, the fastest growing lineages were subjected to continuous sub-culturing in the presence of methylamine and weekly UV mutagenesis (as described above). When the growth rate in the presence of methylamine was comparable to the growth rate in the absence of methylamine, individual colonies were obtained by plating on solid selective media containing methylamine. Colonies showing rapid growth (i.e. fastest visual appearance and largest colony size relative to the approximate average size of colonies on the plate) were picked and assayed for L-asparagine degradation activity. Colonies exhibiting high activity were then further sub-cultured and mutagenized with progressively more methylamine (0.05 g/L to 12 g/L methylamine) in order to increase selective pressure, and thus improve L-asparagine degradation activity. Of note, mutagenizing at different stages in the sub-culturing timeline continuously created new lineages. Only those lineages showing improved L-asparagine degradation activity, relative to the direct predecessor culture, were evolved further.

As a control, a lineage of wild-type yeast that was never mutagenized was kept. This lineage allowed determination if adaptive evolution alone (without mutagenesis) was sufficient to generate the desired phenotype (fully derepressed ASP3), or if the acquired phenotype was a consequence of the evolutionary engineering approach (i.e. providing genetic variability to select upon by UV mutagenesis).

AR Yeast Degrade Asparagine Under NCR Conditions

The expression of ASP3, and thus the ability of baker's yeast to degrade asparagine, is repressed under most growth conditions. In order to maximize the functionality of the AR strains, it was crucial to disrupt the normal NCR mechanisms controlling ASP3 expression. As such, AR strains should degrade asparagine even when grown in nutrient rich media. To test the functionality of the adapted yeast, their ability to degrade asparagine relative to the non-adapted wild-type parent strain was compared.

Figure 2:
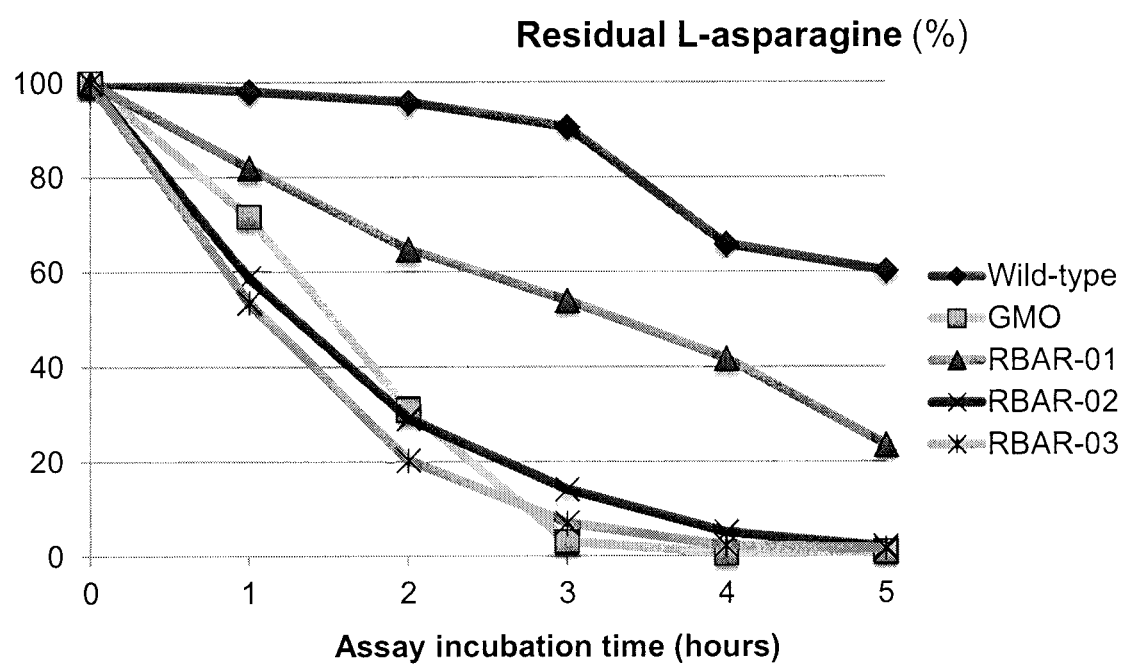
FIG. 2 shows AR yeast strains degrade L-asparagine even when grown in rich media. The wild-type strain, the AR strains (RBAR-01, RBAR-02, and RBAR-03), and a GMO control strain engineered to overexpress ASP3, were grown in YEG overnight (18 hours at 30° C.) before inoculation of $2 \times 10^7$ cells into 5 mL of fresh YEG supplemented with 0.6 g/L L-asparagine. Cells were incubated in YEG+L-asparagine for various time points before heat inactivation at 80° C. Residual L-asparagine concentration in each sample was measured by colorimetric enzymatic assay kit. Data are representative of duplicate experiments.

From the adaptive evolution protocol, three main variants were identified with the desired phenotype (growth on D-asparagine in the presence of methylamine) —RBAR-01, RBAR-02, and RBAR-03. When these strains were tested for asparagine degradation activity, each of the strains exhibited high levels of asparagine breakdown even when grown under nutrient rich (repressive) conditions (FIG. 2). Compared to the wild-type—which showed no appreciable activity up to three hours, and only minimal activity afterwards (greater than 60% residual L-asparagine) —high levels of L-asparagine degradation activity were observed in each of the AR strains, even with as little as one hour of assay time (RBAR-01: 82% L-asparagine remaining at 1 hr; RBAR-02: 59% L-asparagine remaining at 1 hr; RBAR-03: 54% L-asparagine remaining at 1 hr). Importantly, RBAR-02 and RBAR-03 performed substantially better at the one and two-hour marks when compared to a GMO control strain engineered to constitutively express ASPS. This supports the idea that adaptive evolution can often result in functional solutions that are superior to human-directed reverse engineering. Moreover, these data suggest that the adaptively evolved AR yeast will have enhanced utility in industry where short incubation times—which offer economic and food safety benefits—are often desired. Taken together, FIGS. 1 and 2 indicates that the adaptive evolution protocol used successfully altered normal NCR conditions such that the AR yeast degrade asparagine even when grown in rich media (YEG). Importantly, all three of the AR variants originated from separate mutagenesis lineages, thus it is likely that their phenotypes—and associated mechanisms of action—evolved independently.

Iterative Adaptive Evolution is Critical for Generation of the AR Strains

As previously discussed, the single round selection strategy of Kamerud and Roon is not applicable to industrial baker's yeast strains. Thus, a novel, iterative adaptive evolutionary strategy was developed to obtain AR strains with the ability to degrade L-asparagine. The goal of this novel strategy was to slowly increase selective pressure over time, in conjunction with repeated mutagenesis, so as to achieve sufficient genetic diversity to allow for full ASP3 expression—and therefore asparagine breakdown—in otherwise repressive conditions.

Figure 3:
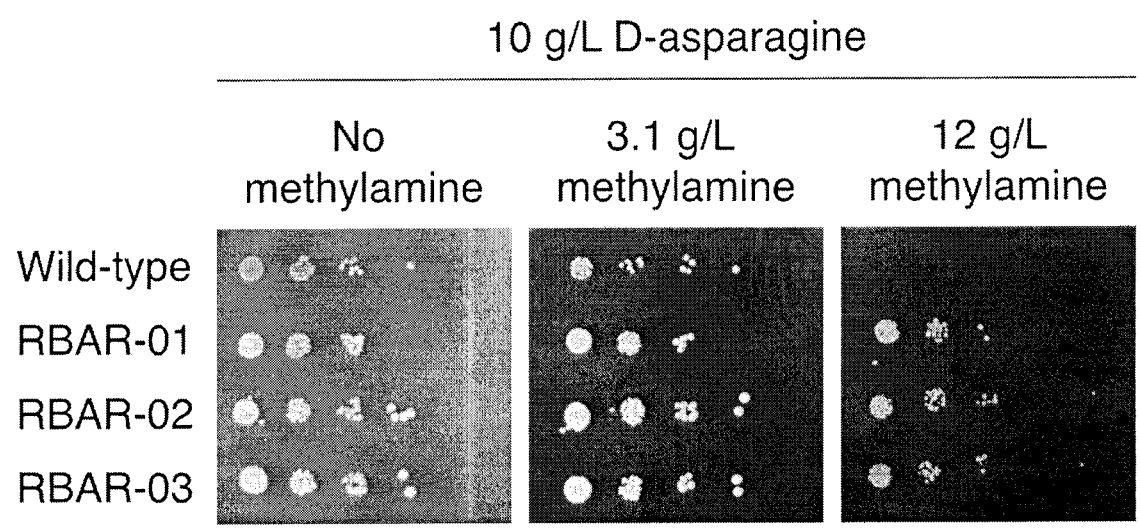
FIG. 3 shows that iterative adaptive evolution is required to generate the AR yeast strains. The wild-type strain as well as the AR strains (RBAR-01, RBAR-02, and RBAR-03) were plated on non-selective media (YEG+D-asparagine), mildly selective media used by Kamerud and Roon (YEG+D-asparagine+3.1 g/L methylamine), and highly selective media used in this study (YEG+D-asparagine+12 g/L methylamine). Equal numbers of cells for each strain spotted in 10-fold serial dilutions. Plates were incubated at 30° C. for four days. Data are representative of triplicate experiments

To confirm the necessity of this iterative process for developing AR strains, the growth of the final AR strains, as well as their wild-type parent, was tested under differing degrees of selective pressure. The strains were plated on minimally-selective media (YEG+D-asparagine), the moderately selective media used by Kamerud and Roon (YEG+D-asparagine+3.1 g/L methylamine), and the highly selective media used in this study (YEG+D-asparagine+12 g/L methylamine). As expected, all of the strains grew equally well in the non-selective conditions (FIG. 3, left plate), but only the AR strains were capable of growing in the most selective conditions (FIG. 3, right plate). Consistent with the previous results, the parent strain was capable of growing on the mildly selective conditions, albeit more slowly than the adaptively evolved AR strains (FIG. 3, middle plate). This growth differential is indicative of the evolutionary changes of the AR strains that enable them to grow successfully in the more highly selective environment. Taken together, these data highlight the necessity of iteratively increasing selective pressure so as to select for successive genetic diversity (evolution) over time. Indeed, only this iterative approach was capable of generating industrial baker's yeast strains capable of growing under highly selective conditions and, as a result, imparting the unique AR phenotype.

Figure 4:
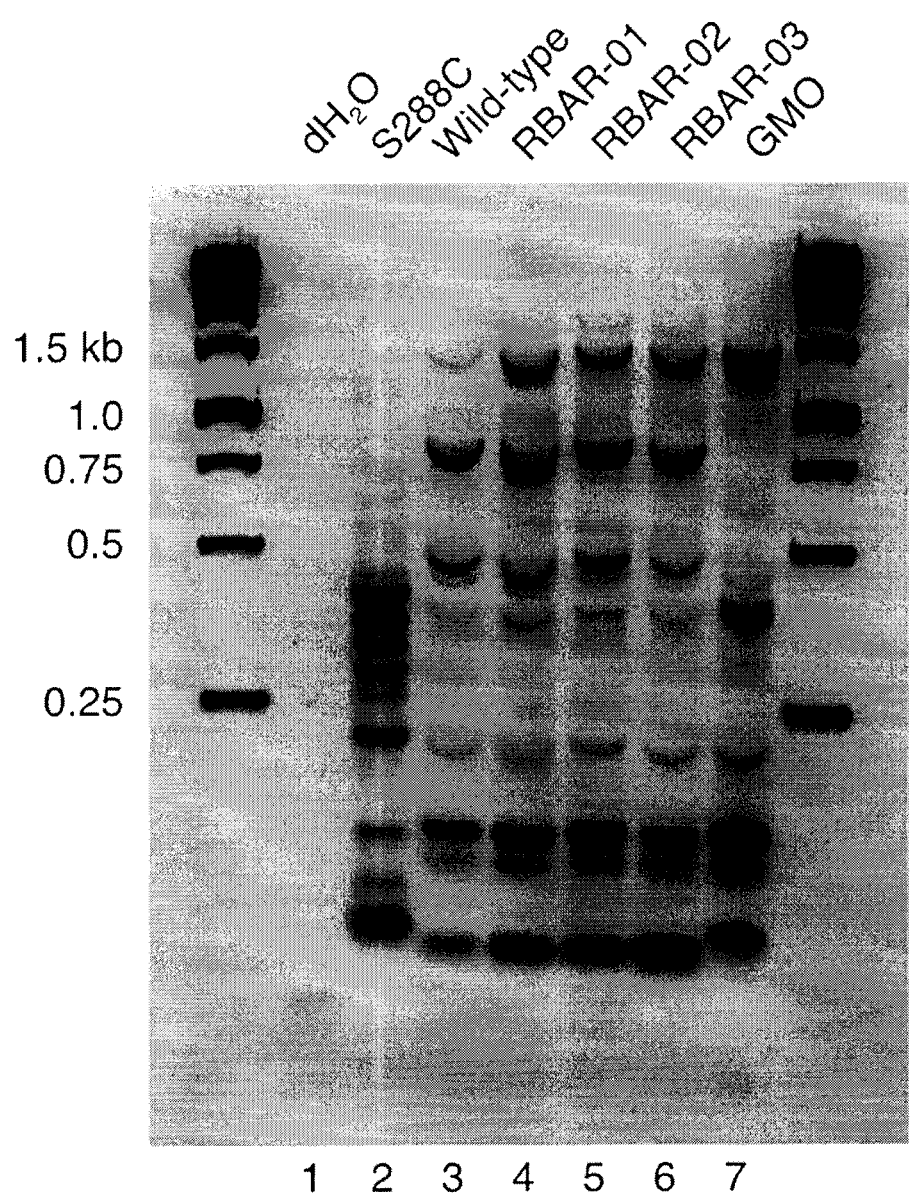
FIG. 4 shows AR yeast strains are evolutionarily derived from their wild-type parent. Inter-delta PCR fingerprinting was used to compare the heritage of the AR yeast strains to their wild-type parent strain. Genomic DNA was extracted from overnight cultures of each of the strains and used as a template for inter-delta PCR as previously described (61). Amplicons were visualized by agarose gel electrophoresis. Data are representative of duplicate experiments.

AR Yeast Strains are Functionally Distinct, Evolutionarily Adapted Descendants of the Wild-Type Strain Directed adaptive evolution allows for the highly specific development of novel phenotypes (e.g. constitutive asparagine degradation). Having demonstrated the evolved phenotype of the AR strains (FIGS. 2 and 3), it became important to ensure these strains were indeed descendants of the wild-type strain, rather than any contaminant strain acquired during culturing. In order to confirm the lineage of the AR strains (RBAR-01, RBAR-02, and RBAR-03), inter-delta fingerprinting PCR was used to type each AR strain against the wild-type parent. Delta sequences that flank the TY1 and TY2 retrotransposons are dispersed throughout the yeast genome. Due to the high mutation rate in these retrotransposons, amplification of intra-delta sequences results in a mixture number and sized bands that can be used to identify specific yeast strains (61). Inter-delta fingerprinting of RBAR-01, RBAR-02, and RBAR-03 amplified the identical number, size distribution, and relative intensity of bands, as compared to the wild-type strain (FIG. 4, compare lanes 3, 4, 5, and 6). This suggests that all of the adapted AR strains are derived from the same parent strain, thus making it likely that they will share similar properties e.g. growth kinetics, vitality, and suitability for industrial baking use. Importantly, the wild-type and AR strains typed differently than the non-related S288C and GMO asparagine degrading yeast control strains (FIG. 4, lanes 1 and 7).

AR Strains Constitutively Express Asparaginase II as Well as Degrade L-Asparagine The NCR system of yeast allows cells to utilize complex nitrogen sources in the most efficient way possible. That is, when multiple sources of differing quality are available, NCR regulates catabolic gene expression such that cells preferentially utilize the highest quality source available before moving onto the next source. Indeed, rich growth media such as YEG contains a complex mixture of a variety of nitrogen sources including ammonium, free amino acids, peptides, and proteins. Consequently, during yeast growth in YEG the quantity and quality of nitrogen available—as well as NCR activity—is in constant flux. As such, although the AR strains exhibited a highly enhanced ability to degrade L-asparagine when grown overnight in YEG (FIG. 2), it remained possible that asparagine breakdown was restricted to the specific nitrogen environment at this timepoint.

To test if ASP3 gene expression—and consequent L-asparagine degradation activity—was specific to a specific timepoint or instead constitutive, a timecourse experiment was performed in which yeast were sampled throughout a 24 hour period. After initial overnight culturing, an equal number of cells of each strain were inoculated into fresh YEG cultures and grown for 24 hours. Samples from each strain were taken at six-hour intervals in order to measure both L-asparagine breakdown (standard 1 hr assay), as well as ASP3 gene expression via qPCR.

Figure 5:
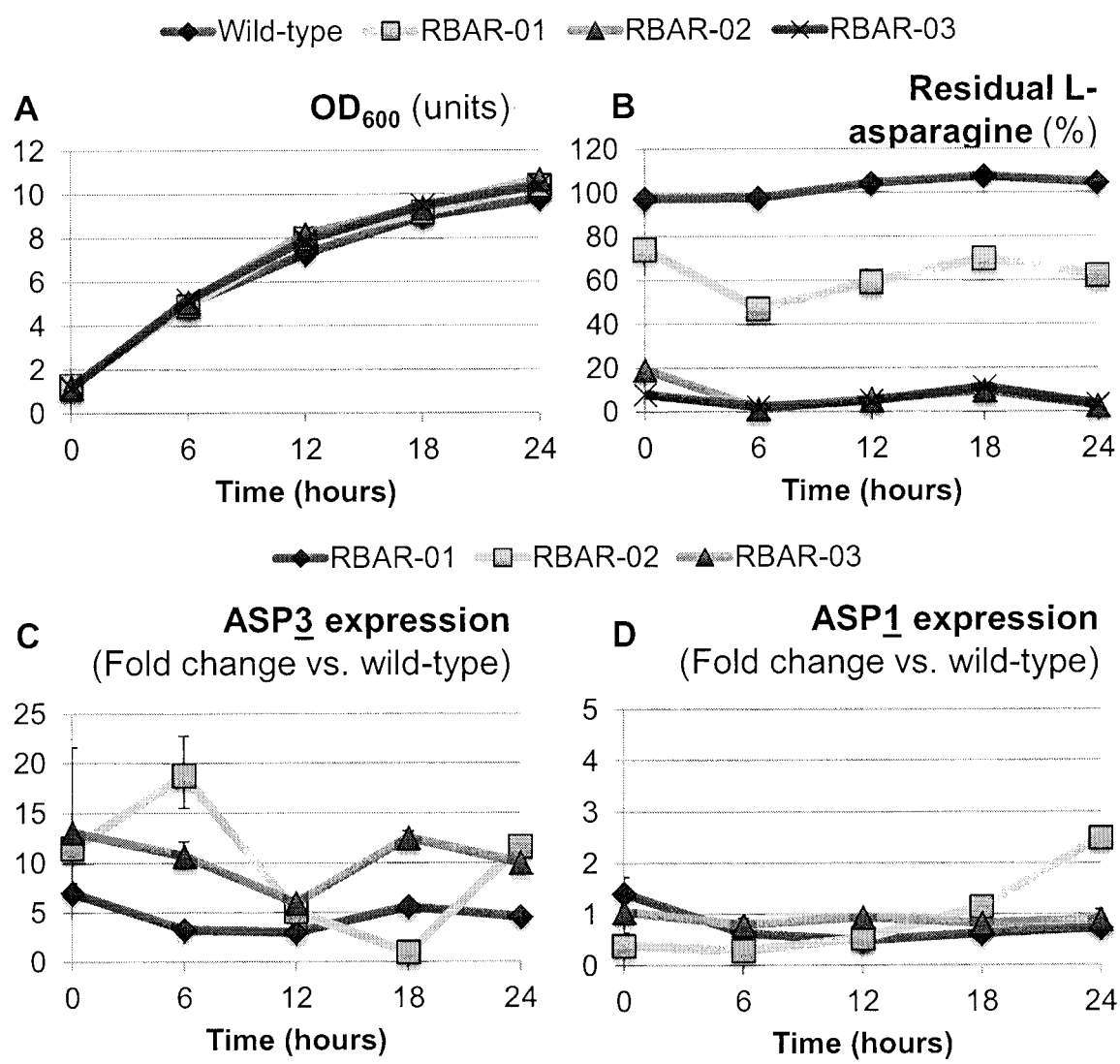
FIG. 5 shows AR yeast strains constitutively degrade L-asparagine and constitutively express the cell-wall associated Asparaginase II (ASP3). The AR yeast strains (RBAR-01, RBAR-02, and RBAR-03), as well as their wild-type parent, were sampled every six hours during growth in YEG. Data are representative of duplicate experiments. A) The growth rate of each strain was tracked by $OD_{600}$ measurement. B) The L-asparagine degradation activity of each strain was measured by a standardized L-asparagine degradation assay (1 hour assay incubation time). C) The relative expression of ASP3 in each strain was measured in technical triplicate by qPCR of cDNA reverse transcribed from isolated total RNA. ASP3 fold change values were calculated using the ΔΔCt method and normalized against ACT1 and wild-type ASP3. D) The relative expression of ASP1 in each strain was measured in technical triplicate by qPCR of cDNA reverse transcribed from isolated total RNA. ASP1 fold change values were calculated using the ΔΔCt method and normalized against ACT1 and wild-type ASP1.

As shown in FIG. 5A, all of the strains grew at comparable rates, allowing the harvest of equal numbers of cells at each timepoint.

In terms of L-asparagine breakdown, both RBAR-02 and RBAR-03 were capable of completely degrading L-asparagine throughout the time course (less than 10% residual L-asparagine), while RBAR-01 had a moderate ability to catabolize L-asparagine during the same time (average of 60% residual L-asparagine). Importantly, the wild-type strain did not exhibit any appreciable L-asparagine breakdown at any point during the experiment (FIG. 5B). Of note, these data are consistent with the L-asparagine degradation observed previously in FIG. 2.

When assayed for ASP3 expression, all of the AR strains exhibited constitutive expression of ASP3 (FIG. 5C). Averaged across all timepoints, RBAR-01, RBAR-02, and RBAR-03 expressed 4.7, 9.6, and 10.5-fold more ASP3 than wild-type, respectively (FIG. 5C). Interestingly, the relative magnitude of the constitutive expression mirrored each strain's ability to degrade L-asparagine throughout the time course (compare FIGS. 5B and 5C). Finally, ASP1 expression in all of the AR strains was not changed compared to wild-type (FIG. 5D), indicating that the observed L-asparagine degradation is the result of the cell-wall associated Asparaginase II (ASP3), rather than the cytosolic Asparaginase I (ASP1). Taken together, these data also indicate that the AR strains constitutively express ASP3 and constitutively degrade L-asparagine as a result of their adaptive evolution.

AR Strains Exhibit Enhanced and Unique Asparaginase II Kinetics

Figure 6:
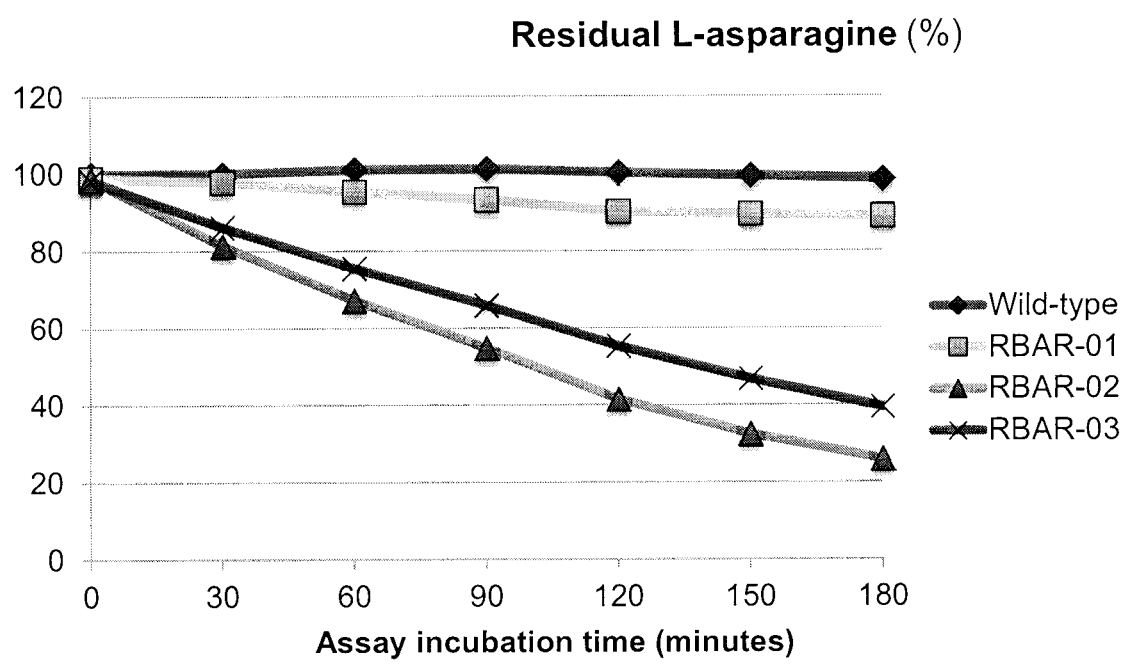
FIG. 6 shows the kinetics of L-asparagine degradation differs between AR yeast strains. The wild-type strain, as well as the AR strains (RBAR-01, RBAR-02, and RBAR-03) were grown in YEG overnight (18 hours at 30° C.) before inoculation of $2\times10^7$ cells into 5 mL of fresh YEG supplemented with 0.6 g/L-asparagine. Cells were incubated in YEG+L-asparagine for various time points before heat inactivation at 80° C. Residual L-asparagine concentration in each sample was measured by colorimetric enzymatic assay kit. Data are representative of duplicate experiments.

Asparagine catabolism produces aspartic acid and ammonia, both of which can be converted to off-flavor compounds such as pyrazines during high temperature cooking. Thus, in certain food production applications, it may be beneficial to utilize an AR yeast with sub-maximal levels of Asparaginase II activity so as to avoid off-flavor production. To test the Asparaginase II kinetics in each AR yeast strain, overnight cultures were inoculated into YEG media containing L-asparagine to a fixed cell number. Samples were then taken at 30 minute intervals and remaining L-asparagine was assayed. While all three AR strains exhibited L-asparagine breakdown compared to wild-type control, L-asparagine breakdown kinetics were not equal amongst the AR strains (FIG. 6). More specifically, RBAR-01 has a lower rate of L-asparagine breakdown compared to both RBAR-02 and RBAR-03 (RBAR-01: 82% L-asparagine remaining at 90 min), while RBAR-02 and RBAR-03 were similar (RBAR-02: 54% L-asparagine remaining at 90 min; RBAR-03: 66% L-asparagine remaining at 90 min). These data are consistent with the L-asparagine breakdown observed in FIG. 2 and, taken in conjunction with the rest of the data, support the phenotype in the adaptively evolved AR yeast.

AR Strains Exhibit Differential Gene Expression of NCR Regulated Genes

By virtue of its inherent non-specific nature, random mutagenesis and adaptive evolution has the ability to change the expression of many different genes, in addition to the gene of interest. Having determined that the AR yeast strains indeed constitutively express ASP3 and degrade L-asparagine in the presence of quality nitrogen sources in otherwise active NCR conditions (FIGS. 2, 5, and 6), the inventors sought to evaluate the global gene expression profiles of the AR yeast.

To do so, a fixed number of cells from overnight cultures were inoculated into fresh YEG media and the cultures were incubated for six hours. Total RNA was then extracted from the samples and RNA sequencing libraries were constructed from reverse-transcribed cDNA (poly dT priming). Sequencing was performed on an Illumina HiSeq2500 High Output mode platform in a 2×100 bp paired-end configuration.

On average, 67.5 million reads per strain were obtained which equals 6,818 megabases and approximately 560-fold coverage (assuming a 12 Mb haploid genome). The sequencing data was generally of very high quality, with 94% of Q scores greater than or equal to 30, and a mean Q score of 37.

Figure 7:
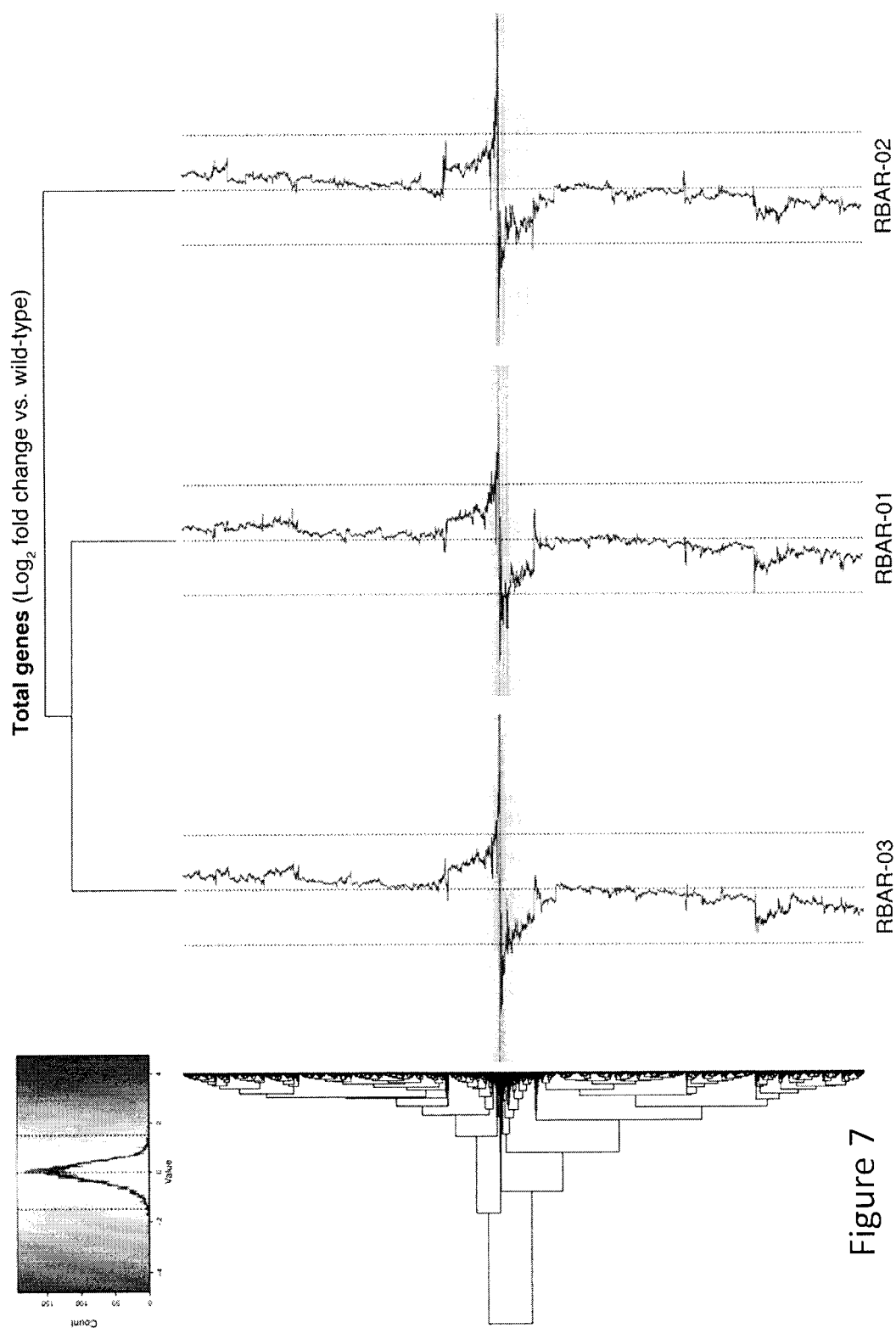
FIG. 7 shows a minimal number of genes are differentially expressed globally in the AR yeast strains. Total RNA was harvested from wild-type and AR yeast strains (RBAR-01, RBAR-02, and RBAR-03) during exponential growth in YEG. RNA sequencing libraries (TruSeq v3) —prepared from total RNA—were sequenced on an Illumina HiSeq2500 High Output mode platform in a 2×100 bp paired-end configuration. Raw reads were filtered for quality and mapped to the S288C reference genome. $Log_2$ fold change values (relative to wild-type) are shown for each of the 6,604 yeast ORFs (verified, uncharacterized, and dubious). Dotted lines are drawn at +1.5, 0, and −1.5 for reference. The traced line within each row is the actual fold change value for each gene. Hierarchical clustering was used to group both gene clusters and strains.
Figure 8A:
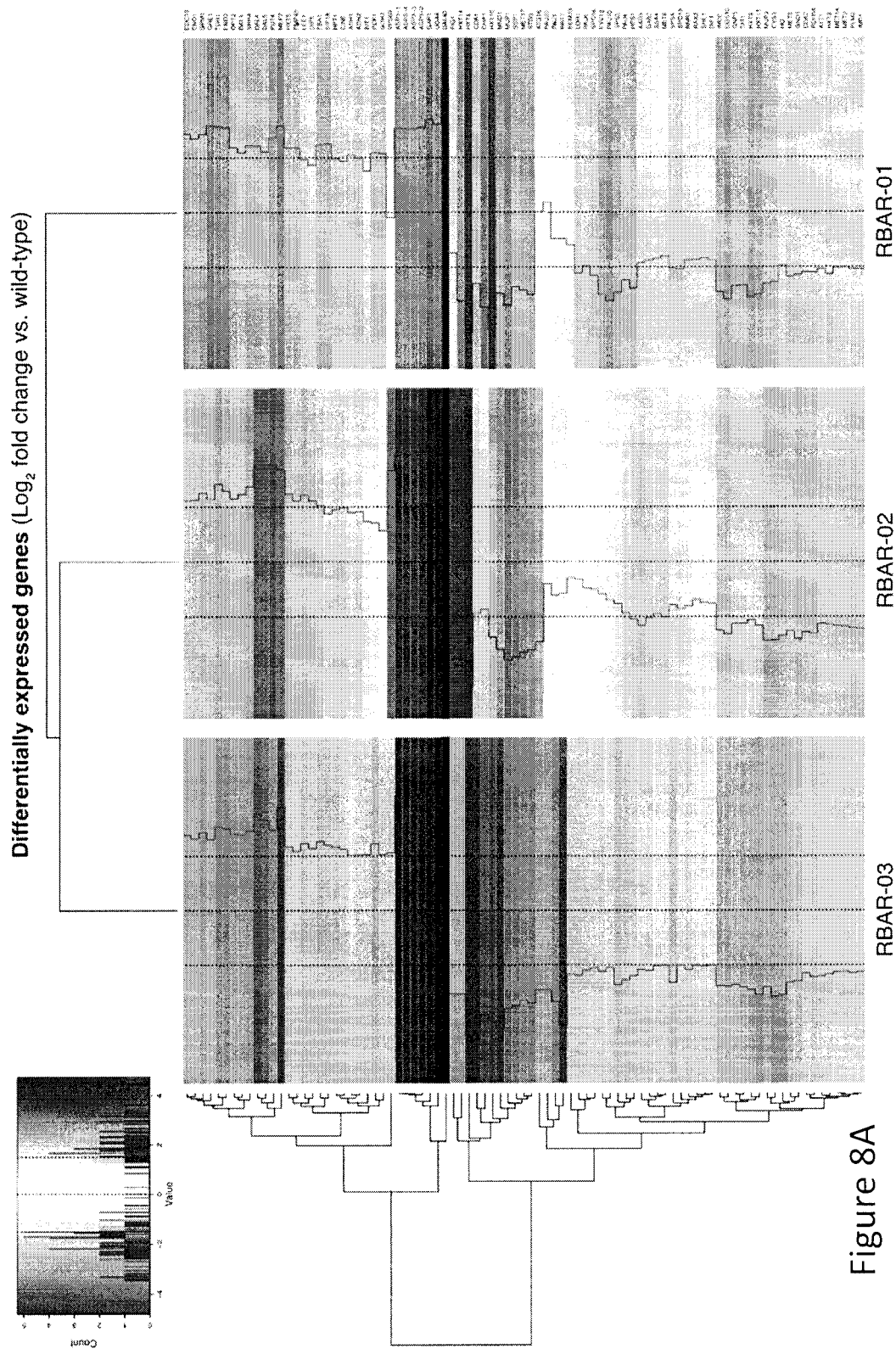
FIG. 8 shows many differentially expressed genes are common to each of the AR yeast strains. Total RNA was harvested from wild-type and AR yeast strains (RBAR-01, RBAR-02, and RBAR-03) during exponential growth in YEG. RNA sequencing libraries (TruSeq v3) —prepared from total RNA—were sequenced on an Illumina HiSeq2500 High Output mode platform in a 2×100 bp paired-end configuration. Raw reads were filtered for quality and mapped to the S288C reference genome. A) $Log_2$ fold change values (relative to wild-type) are shown for each of the differentially expressed genes (≥|1.5| log 2 fold change & ≥100 counts in the wild-type yeast). Dotted lines are drawn at +1.5, 0, and −1.5 for reference. The traced line within each row is the actual fold change value for each gene. Hierarchical clustering was used to group both gene clusters and strains. B) Venn diagram of the overlap between differentially expressed genes in each of the AR yeast strains.
Figure 8B:
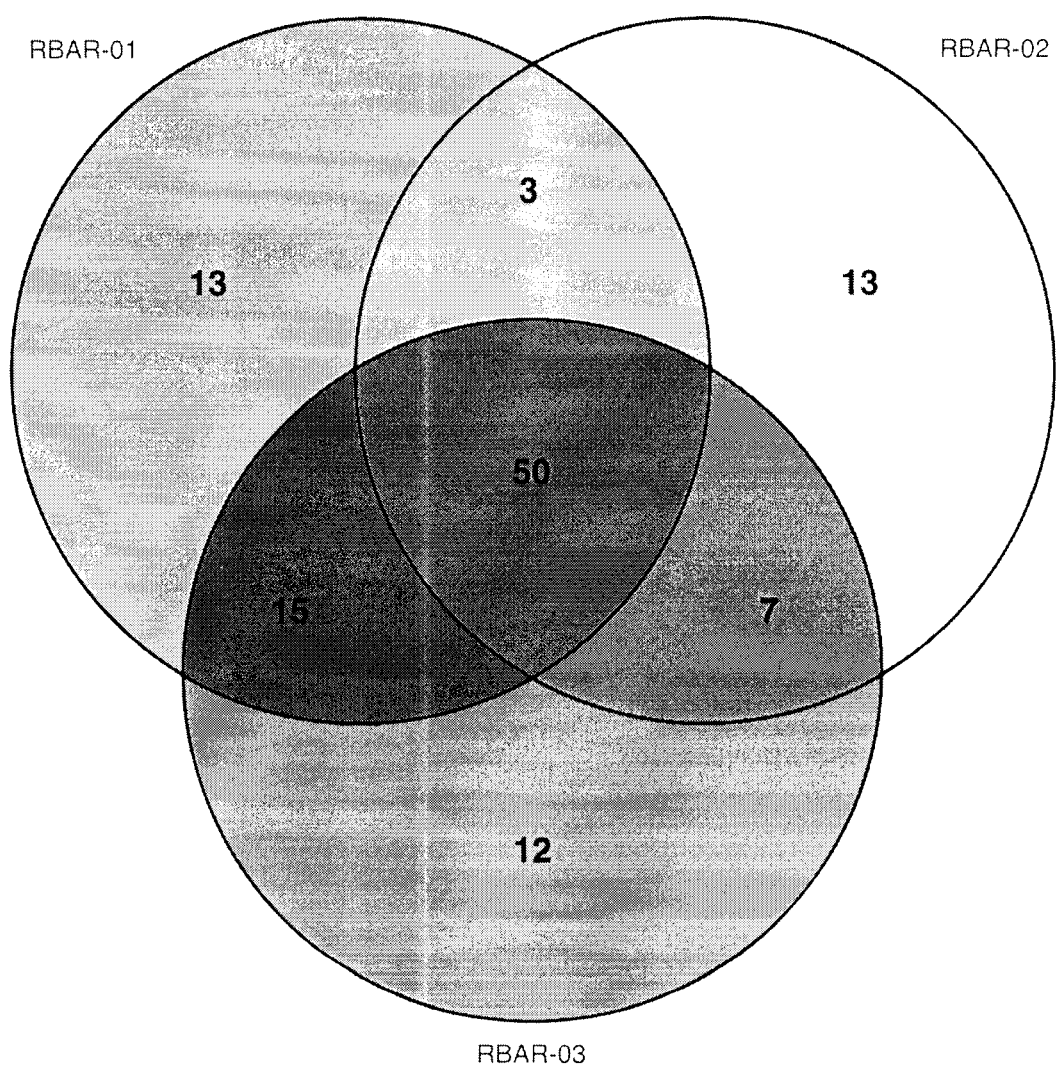

Raw reads for each strain were trimmed and filtered for quality (Q score greater than or equal to 30) before mapping to the S288C reference genome. On average 97.6% of reads were successfully aligned. Aligned reads were used to construct per gene read counts that then formed the basis of differential gene expression (DEG) analysis. For each AR strain, the log 2 fold change of each gene relative to the wild-type was calculated (FIG. 7). Genes with fold change values of magnitude greater than 1.5 and wild-type read counts of at least 100 were considered differentially expressed (DE). FIG. 8A and Table 8 compare the expression levels of the DEG in each AR strain. By these criteria for DEG, 81 (1.6%), 73 (1.4%), and 84 (1.6%) DEG (out of 5,121 verified S288C ORFs) were observed in each of RBAR-01, RBAR-02, and RBAR-03, respectively. Moreover, 50 out of 113 (44.2%) DEG were common to all three strains, while 75 (66.4%) DEG were common to at least two of the AR strains (FIG. 8B). By RNAseq analysis ASP3 was amongst the top upregulated genes in each of the AR strains (Table 8). Indeed, ASP3 was upregulated 4.9, 7.8 and 8.9-fold in RBAR-01, RBAR-02, and RBAR-03, respectively, which is consistent with the L-asparagine degradation data and qPCR data obtained in FIGS. 5B and 5C.

Figure 9A:
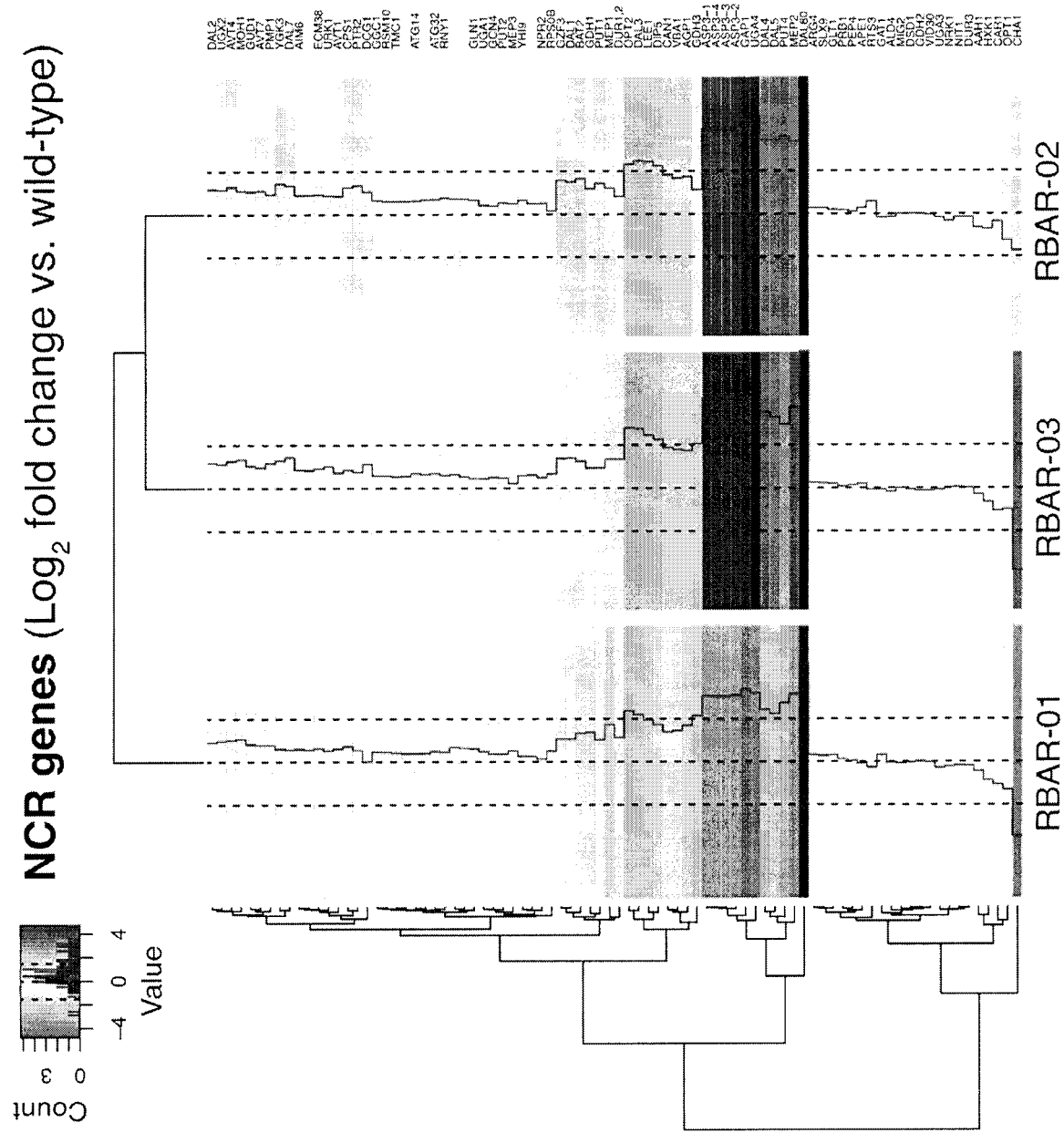
FIG. 9 shows many NCR genes and amino acid transporters are differentially expressed in each of the AR yeast strains. Total RNA was harvested from wild-type and AR yeast strains (RBAR-01, RBAR-02, and RBAR-03) during exponential growth in YEG. RNA sequencing libraries (TruSeq v3) —prepared from total RNA—were sequenced on an Illumina HiSeq2500 High Output mode platform in a 2×100 bp paired-end configuration. Raw reads were filtered for quality and mapped to the S288C reference genome. A) $Log_2$ fold change values (relative to wild-type) are shown for each of the annotated NCR genes (71). B) $Log_2$ fold change values (relative to wild-type) are shown for each of the annotated amino acid transporter genes (71). A and B) Dotted lines are drawn at +1.5, 0, and −1.5 for reference. The traced line within each row is the actual fold change value for each gene. Hierarchical clustering was used to group both gene clusters and strains.

In addition to ASP3, DEG analysis revealed substantial differential regulation of many NCR genes (FIG. 9A). In total, 15 (19.0%), 15 (19.0%), and 17 (21.2%) of the 79 known NCR controlled genes were differentially expressed in RBAR-01, RBAR-02, and RBAR-03, respectively. All of these enrichments were highly statistically significant by Fisher's exact test (p≤0.0001).

Finally, to analyze the affected genetic pathways and networks in the AR yeast from a global perspective, gene ontology analysis of the DEG was also performed in each of the AR strains (Table 9). While many biological processes, cellular compartments, and molecular functions were significantly affected, the most obvious is a wholesale deregulation of nutrient transport in the AR strains, especially amino acid transport (FIG. 9A, Tables 8 and 9). Indeed, many of the top DEG (both up- and down-regulated) are permease enzymes, including UGA4, GAP1, MEP2, DAL4, DAL5, PUT4, OPT2, HXT5, HXT4, HXT10, HXT11, HXT14, HXT9, MUP1, TAT1, MUP3, and GNP1 (FIG. 9A and Table 8).

Taken together, these data indicate that the adaptively evolved AR yeast exhibit substantial differential gene expression profiles relative to their non-evolved parent. Furthermore, the major pathways affected in the AR yeast include NCR control and amino acid transport.

Total RNA was harvested from wild-type and AR yeast strains (RBAR-01, RBAR-02, and RBAR-03) during exponential growth in YEG. RNA sequencing libraries (TruSeq v3) —prepared from total RNA—were sequenced on an Illumine HiSeq2500 High Output mode platform in a 2×100 bp paired-end configuration. Raw reads were filtered for quality and mapped to the S288C reference genome. $Log_2$ fold change values (relative to wild-type) were calculated for each of the 6,604 yeast ORFs (verified, uncharacterized, and dubious). Differentially expressed genes were called according to the following criteria: ≥|1.5| log 2 fold change & ≥100 counts in the wild-type yeast. See Table 8.

TABLE 8

Differentially expressed genes in the AR yeast strains.

| Gene ID | Gene Name | Description | RBAR-01 $log_2$ FC[a] | RBAR-02 $log_2$ FC | RBAR-03 $log_2$ FC |
|---|---|---|---|---|---|
| Upregulated genes (≥1.5 $log_2$) | | | | | |
| YKR034W | DAL80 | Negative regulator of multiple nitrogen degradation pathways | 3.408 | 4.596 | 4.776 |
| YDL210W | UGA4 | GABA (gamma-aminobutyrate) permease | 2.399 | 3.374 | 3.658 |
| YKR039W | GAP1 | General amino acid permease | 2.528 | 3.277 | 3.254 |
| YLR157C | ASP3-2 | Cell-wall L-asparaginase II involved in asparagine catabolism | 2.323 | 3 | 3.172 |
| YLR160C | ASP3-4 | Cell-wall L-asparaginase II involved in asparagine catabolism | 2.282 | 2.955 | 3.161 |
| YLR155C | ASP3-1 | Cell-wall L-asparaginase II involved in asparagine catabolism | 2.298 | 2.959 | 3.156 |
| YLR158C | ASP3-3 | Cell-wall L-asparaginase II involved in asparagine catabolism | 2.283 | 2.943 | 3.132 |
| YNL142W | MEP2 | Ammonium permease involved in pseudohyphal growth | 2.359 | 2.505 | 2.847 |
| YIR028W | DAL4 | Allantoin permease | 1.823 | 2.557 | 2.655 |
| YJR152W | DAL5 | Allantoate permease | 1.664 | 2.559 | 2.474 |
| YJL052W | TDH1 | Glyceraldehyde-3-phosphate dehydrogenase (GAPDH), isozyme 1 | 2.351 | 2.124 | 2.297 |
| YHR174W | ENO2 | Enolase II, a phosphopyruvate hydratase | 2.325 | 1.933 | 2.257 |
| YOR348C | PUT4 | Proline permease | 2.046 | 2.677 | 2.222 |
| YLR164W | SHH4 | Putative alternate subunit of succinate dehydrogenase (SDH) | 1.832 | 2.053 | 2.188 |
| YKL152W | GPM1 | Tetrameric phosphoglycerate mutase | 2.146 | 1.884 | 2.135 |
| YPR194C | OPT2 | Oligopeptide transporter | 1.773 | 1.723 | 2.099 |
| YAL038W | CDC19 | Pyruvate kinase | 2.148 | 1.671 | 2.085 |
| YIR032C | DAL3 | Ureidoglycolate lyase | 1.638 | 1.847 | 2.085 |
| YGR254W | ENO1 | Enolase I, a phosphopyruvate hydratase | 2.014 | 1.688 | 1.976 |
| YPL223C | GRE1 | Hydrophilin essential in desiccation-rehydration process | 2.376 | 1.71 | 1.949 |
| YKL060C | FBA1 | Fructose 1,6-bisphosphate aldolase | 1.848 | 1.536 | 1.89 |
| YPL054W | LEE1 | Zinc-finger protein of unknown function | 1.449 | 1.823 | 1.844 |
| YKR097W | PCK1 | Phosphoenolpyruvate carboxykinase | 1.626 | 1.055 | 1.83 |
| YMR175W | SIP18 | Phospholipid-binding hydrophilin | 1.875 | 1.308 | 1.795 |
| YHR096C | HXT5 | Hexose transporter with moderate affinity for glucose | 1.767 | 1.855 | 1.756 |
| YDR399W | HPT1 | Dimeric hypoxanthine-guanine phosphoribosyltransferase | 1.468 | 1.434 | 1.741 |
| YPL265W | DIP5 | Dicarboxylic amino acid permease | 1.288 | 1.671 | 1.702 |
| YOR028C | CIN5 | Basic leucine zipper (bZIP) transcription factor of the yAP-1 family | 1.4 | 1.476 | 1.68 |
| YDL222C | FMP45 | Integral membrane protein localized to mitochondria | 1.767 | 1.67 | 1.618 |
| YAL062W | GDH3 | NADP(+)-dependent glutamate dehydrogenase | 1.606 | 0.843 | 1.543 |
| YEL065W | SIT1 | Ferrioxamine B transporter | 1.134 | 1.1 | 1.54 |
| YMR303C | ADH2 | Glucose-repressible alcohol dehydrogenase II | 1.49 | 1.362 | 1.523 |
| YOL086C | ADH1 | Alcohol dehydrogenase | 1.571 | 1.342 | 1.522 |
| Downregulated genes (≥−1.5 $log_2$) | | | | | |
| YCR106W | RDS1 | Putative zinc cluster transcription factor | — | — | −8.722 |
| YCR104W | PAU3 | Member of the seripauperin multigene family | −6.071 | — | −6.925 |
| YHR092C | HXT4 | High-affinity glucose transporter | −3.317 | −3.409 | −3.456 |
| YLR307W | CDA1 | Chitin deacetylase | −1.954 | −1.404 | −3.392 |
| YGL183C | MND1 | Protein required for recombination and meiotic nuclear division | −2.213 | −2.393 | −3.269 |
| YFL011W | HXT10 | Putative hexose transporter | −3.191 | −2.056 | −3.044 |
| YCL064C | CHA1 | Catabolic L-serine (L-threonine) deaminase | −2.595 | −1.296 | −2.881 |
| YGR055W | MUP1 | High affinity methionine permease | −2.547 | −2.678 | −2.69 |
| YHR184W | SSP1 | Protein involved in the control of meiotic nuclear division | −2.031 | −2.597 | −2.585 |
| YGL184C | STR3 | Peroxisomal cystathionine beta-lyase | −2.243 | −2.394 | −2.528 |
| YJL223C | PAU1 | Member of the seripauperin multigene family | −0.731 | −0.918 | −2.492 |
| YLR303W | MET17 | O-acetyl homoserine-O-acetyl serine sulfhydrylase | −2.128 | −2.467 | −2.455 |
| YAL012W | CYS3 | Cystathionine gamma-lyase | −1.912 | −2.143 | −2.355 |
| YDL227C | HO | Site-specific endonuclease | −1.468 | −2.012 | −2.322 |
| YOL156W | HXT11 | Putative hexose transporter that is nearly identical to Hxt9p | −2.246 | −1.749 | −2.322 |
| YBR040W | FIG1 | Integral membrane protein required for efficient mating | −1.11 | −3.297 | −2.285 |
| YNL318C | HXT14 | Protein with similarity to hexose transporter family members | −2.432 | −3.297 | −2.285 |
| YJL219W | HXT9 | Putative hexose transporter that is nearly identical to Hxt11p | −2.316 | −1.597 | −2.17 |
| YBR069C | TAT1 | Amino acid transporter for valine, leucine, isoleucine, and tyrosine | −2.001 | −1.691 | −2.105 |
| YHL036W | MUP3 | Low affinity methionine permease | −1.963 | −2.155 | −2.098 |
| YNR075W | COS10 | Protein of unknown function | −2.381 | −1.968 | −2.089 |
| YHR216W | IMD2 | Inosine monophosphate dehydrogenase | −2.175 | −1.872 | −2.075 |
| YDR522C | SPS2 | Protein expressed during sporulation | −2.191 | −1.149 | −2.044 |
| YDR508C | GNP1 | High-affinity glutamine permease | −2.019 | −1.698 | −2.035 |
| YJR137C | MET5 | Sulfite reductase beta subunit | −1.762 | −1.89 | −1.978 |
| YOR313C | SPS4 | Protein whose expression is induced during sporulation | −1.539 | −1.182 | −1.977 |

TABLE 8-continued

Differentially expressed genes in the AR yeast strains.

| Gene ID | Gene Name | Description | RBAR-01 log$_2$ FC[a] | RBAR-02 log$_2$ FC | RBAR-03 log$_2$ FC |
|---|---|---|---|---|---|
| YHR183W | GND1 | 6-phosphogluconate dehydrogenase (decarboxylating) | −1.718 | −2.108 | −1.937 |
| YLR461W | PAU4 | Member of the seripauperin multigene family | −1.861 | −1.404 | −1.907 |
| YBR073W | RDH54 | DNA-dependent ATPase | −1.658 | −1.96 | −1.831 |
| YLL063C | AYT1 | Acetyltransferase | −1.563 | −1.686 | −1.809 |
| YOR237W | HES1 | Protein implicated in the regulation of ergosterol biosynthesis | −2.082 | −1.569 | −1.798 |
| YJL038C | LOH1 | Protein involved in outer spore wall assembly | −1.67 | −0.476 | −1.786 |
| YDR345C | HXT3 | Low affinity glucose transporter of the major facilitator superfamily | −1.698 | −1.718 | −1.755 |
| YLR308W | CDA2 | Chitin deacetylase | −1.638 | −1.918 | −1.726 |
| YDR501W | PLM2 | Putative transcription factor, contains Forkhead Associated domain | −1.555 | −1.815 | −1.724 |
| YKL001C | MET14 | Adenylylsulfate kinase | −1.519 | −1.754 | −1.7 |
| YAR073W | IMD1 | Nonfunctional protein with homology to IMP dehydrogenase | −1.574 | −1.838 | −1.7 |
| YNL277W | MET2 | L-homoserine-O-acetyltransferase | −1.52 | −1.766 | −1.689 |
| YOR183W | FYV12 | Protein of unknown function | −2.234 | −0.877 | −1.672 |
| YLR343W | GAS2 | 1,3-beta-glucanosyltransferase | −1.316 | −1.529 | −1.655 |
| YNR076W | PAU6 | Member of the seripauperin multigene family | −1.468 | −0.717 | −1.644 |
| YER070W | RNR1 | Major isoform-large subunit of ribonucleotide-diphosphate reductase | −1.319 | −1.211 | −1.63 |
| YCR107W | AAD3 | Putative aryl-alcohol dehydrogenase | −1.387 | −1.739 | −1.63 |
| YHR153C | SPO16 | Meiosis-specific protein for synaptonemal complex assembly | −1.731 | −0.749 | −1.585 |
| YDR542W | PAU10 | Protein of unknown function | −2.432 | −1.049 | −1.585 |
| YBL031W | SHE1 | Mitotic spindle protein | −1.258 | −1.123 | −1.533 |
| YER103W | SSA4 | Heat shock protein that is highly induced upon stress | −1.269 | −1.409 | −1.527 |
| YER091C | MET6 | Cobalamin-independent methionine synthase | −1.214 | −1.506 | −1.509 |
| YHR014W | SPO13 | Meiotic regulator | −1.573 | −1.286 | −1.509 |
| YLR084C | RAX2 | N-glycosylated protein | −1.304 | −1.042 | −1.508 |
| YLR437C | DIF1 | Protein that regulates nuclear localization of Rnr2p and Rnr4p | −1.316 | −1.143 | −1.506 |

[a]Fold change

Differentially expressed genes identified in Table 8 were analyzed by GO enrichment analysis (Table 9). Enrichment p-values are corrected for multiple testing by the Holm-Bonferroni method.

TABLE 9

Gene ontology (GO) enrichment analysis in the AR yeast strains.

| Gene ontology term | Enrichment p-value | Genes enriched | Percent of DEG[a] | Percent of genome |
|---|---|---|---|---|
| Biological process | | | | |
| aspartate family amino acid metabolic process | 1.8E−06 | 12 | 7.0% | 0.2% |
| oxoacid metabolic process | 3.1E−05 | 25 | 14.5% | 0.5% |
| organic acid metabolic process | 3.2E−05 | 25 | 14.5% | 0.5% |
| carboxylic acid metabolic process | 7.2E−05 | 24 | 14.0% | 0.5% |
| amino acid transmembrane transport | 9.8E−05 | 8 | 4.7% | 0.2% |
| organonitrogen compound metabolic process | 1.2E−04 | 30 | 17.4% | 0.6% |
| organic acid transmembrane transport | 2.1E−04 | 8 | 4.7% | 0.2% |
| hexose transport | 2.4E−04 | 7 | 4.1% | 0.1% |
| monosaccharide transport | 2.4E−04 | 7 | 4.1% | 0.1% |
| sulfur amino acid biosynthetic process | 5.3E−04 | 8 | 4.7% | 0.2% |
| small molecule metabolic process | 6.9E−04 | 32 | 18.6% | 0.6% |
| aspartate family amino acid catabolic process | 9.5E−04 | 5 | 2.9% | 0.1% |
| anion transmembrane transport | 1.0E−03 | 9 | 5.2% | 0.2% |
| asparagine catabolic process | 1.3E−03 | 4 | 2.3% | 0.1% |
| reproductive process in single-celled organism | 2.2E−03 | 13 | 7.6% | 0.3% |
| ascospore formation | 3.6E−03 | 11 | 6.4% | 0.2% |
| cell development | 3.6E−03 | 11 | 6.4% | 0.2% |
| sulfur amino acid metabolic process | 4.0E−03 | 8 | 4.7% | 0.2% |
| organonitrogen compound catabolic process | 4.7E−03 | 11 | 6.4% | 0.2% |
| methionine biosynthetic process | 5.0E−03 | 7 | 4.1% | 0.1% |
| amino acid transport | 5.4E−03 | 8 | 4.7% | 0.2% |
| ascospore wall assembly | 5.4E−03 | 8 | 4.7% | 0.2% |
| spore wall assembly | 5.4E−03 | 8 | 4.7% | 0.2% |
| spore wall biogenesis | 5.4E−03 | 8 | 4.7% | 0.2% |
| ascospore wall biogenesis | 5.4E−03 | 8 | 4.7% | 0.2% |
| developmental process involved in reproduction | 6.1E−03 | 13 | 7.6% | 0.3% |
| single organism reproductive process | 6.1E−03 | 13 | 7.6% | 0.3% |
| sexual sporulation | 6.2E−03 | 11 | 6.4% | 0.2% |
| sexual sporulation resulting in formation of a cellular spore | 6.2E−03 | 11 | 6.4% | 0.2% |

TABLE 9-continued

Gene ontology (GO) enrichment analysis in the AR yeast strains.

| Gene ontology term | Enrichment p-value | Genes enriched | Percent of DEG[a] | Percent of genome |
|---|---|---|---|---|
| fungal-type cell wall assembly | 6.3E−03 | 8 | 4.7% | 0.2% |
| cell wall assembly | 7.3E−03 | 8 | 4.7% | 0.2% |
| alpha-amino acid metabolic process | 8.1E−03 | 14 | 8.1% | 0.3% |
| cellular response to nitrogen starvation | 9.0E−03 | 4 | 2.3% | 0.1% |
| cellular response to nitrogen levels | 9.0E−03 | 4 | 2.3% | 0.1% |
| cellular amino acid metabolic process | 1.1E−02 | 16 | 9.3% | 0.3% |
| carboxylic acid transport | 1.4E−02 | 9 | 5.2% | 0.2% |
| meiotic cell cycle process | 1.4E−02 | 15 | 8.7% | 0.3% |
| anatomical structure morphogenesis | 1.5E−02 | 14 | 8.1% | 0.3% |
| anatomical structure development | 1.5E−02 | 14 | 8.1% | 0.3% |
| methionine metabolic process | 1.5E−02 | 7 | 4.1% | 0.1% |
| serine family amino acid metabolic process | 1.5E−02 | 7 | 4.1% | 0.1% |
| organic acid transport | 1.5E−02 | 9 | 5.2% | 0.2% |
| cysteine metabolic process | 1.5E−02 | 5 | 2.9% | 0.1% |
| cellular component morphogenesis | 1.7E−02 | 10 | 5.8% | 0.2% |
| transmembrane transport | 1.8E−02 | 20 | 11.6% | 0.4% |
| cellular developmental process | 1.9E−02 | 15 | 8.7% | 0.3% |
| nicotinamide nucleotide metabolic process | 2.5E−02 | 9 | 5.2% | 0.2% |
| pyridine nucleotide metabolic process | 2.8E−02 | 9 | 5.2% | 0.2% |
| pyruvate metabolic process | 2.8E−02 | 7 | 4.1% | 0.1% |
| asparagine metabolic process | 3.2E−02 | 4 | 2.3% | 0.1% |
| carbohydrate transport | 3.8E−02 | 7 | 4.1% | 0.1% |
| glycolytic process | 3.9E−02 | 6 | 3.5% | 0.1% |
| gluconeogenesis | 4.7E−02 | 6 | 3.5% | 0.1% |
| Cellular compartment | | | | |
| plasma membrane | 8.4E−08 | 28 | 16.3% | 0.5% |
| cell periphery | 6.3E−07 | 32 | 18.6% | 0.6% |
| cell wall-bounded periplasmic space | 3.0E−03 | 4 | 2.3% | 0.1% |
| membrane | 1.7E−02 | 50 | 29.1% | 1.0% |
| periplasmic space | 2.0E−02 | 4 | 2.3% | 0.1% |
| Molecular function | | | | |
| monosaccharide transmembrane transporter activity | 4.4E−06 | 7 | 4.1% | 0.1% |
| hexose transmembrane transporter activity | 4.4E−06 | 7 | 4.1% | 0.1% |
| sugar transmembrane transporter activity | 3.7E−05 | 7 | 4.1% | 0.1% |
| substrate-specific transporter activity | 4.0E−05 | 21 | 12.2% | 0.4% |
| substrate-specific transmembrane transporter activity | 7.0E−05 | 19 | 11.0% | 0.4% |
| fructose transmembrane transporter activity | 8.5E−05 | 6 | 3.5% | 0.1% |
| mannose transmembrane transporter activity | 8.5E−05 | 6 | 3.5% | 0.1% |
| carbohydrate transmembrane transporter activity | 9.9E−05 | 7 | 4.1% | 0.1% |
| carbohydrate transporter activity | 9.9E−05 | 7 | 4.1% | 0.1% |
| glucose transmembrane transporter activity | 1.3E−04 | 6 | 3.5% | 0.1% |
| amino acid transmembrane transporter activity | 1.8E−04 | 8 | 4.7% | 0.2% |
| L-amino acid transmembrane transporter activity | 2.1E−04 | 6 | 3.5% | 0.1% |
| carboxylic acid transmembrane transporter activity | 2.7E−04 | 9 | 5.2% | 0.2% |
| transmembrane transporter activity | 4.1E−04 | 19 | 11.0% | 0.4% |
| organic acid transmembrane transporter activity | 4.2E−04 | 9 | 5.2% | 0.2% |
| asparaginase activity | 4.9E−04 | 4 | 2.3% | 0.1% |
| transporter activity | 6.8E−04 | 21 | 12.2% | 0.4% |
| galactose transmembrane transporter activity | 1.4E−03 | 4 | 2.3% | 0.1% |
| organic anion transmembrane transporter activity | 1.6E−03 | 9 | 5.2% | 0.2% |
| anion transmembrane transporter activity | 3.1E−03 | 10 | 5.8% | 0.2% |
| neutral amino acid transmembrane transporter activity | 1.2E−02 | 4 | 2.3% | 0.1% |
| hydrolase activity, acting on carbon-nitrogen (but not peptide) bonds, in linear amides | 1.8E−02 | 6 | 3.5% | 0.1% |
| L-proline transmembrane transporter activity | 2.8E−02 | 3 | 1.7% | 0.1% |

[a]Differentially expressed genes

AR Strains are Genetically Distinct from their Non-Adaptively Evolved Parent

Figure 9B:
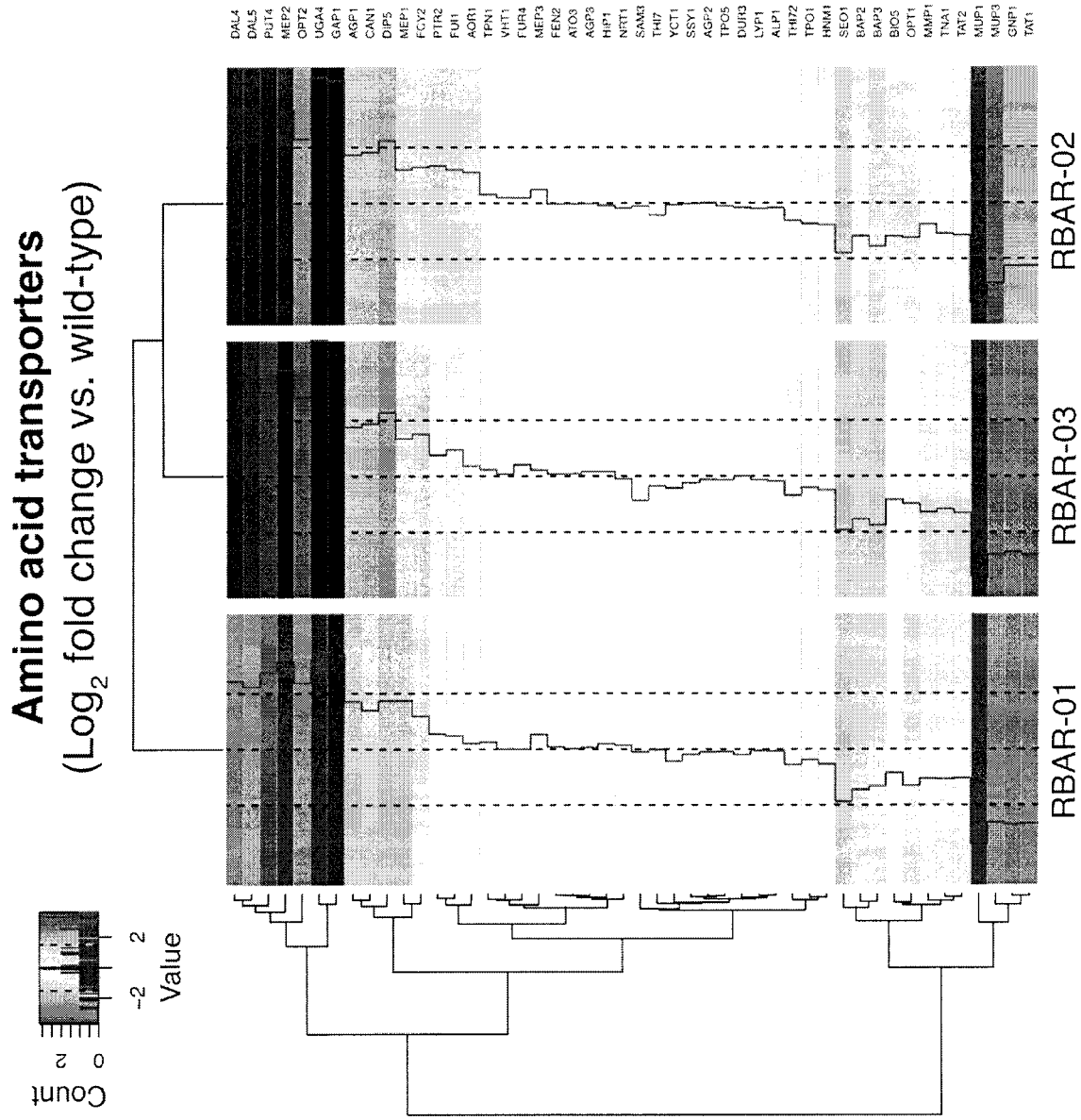

The fundamental principle governing adaptive evolution is the accumulation of mutations that collectively afford an organism with a fitness advantage in a particular environment. Having selected the AR strains based on the ability to constitutively degrade L-asparagine (FIGS. 1, 2, 5, and 6), and having identified subsets of relevant DEGs in the AR strains (FIGS. 7, 8, and 9), the inventors next wanted to examine the AR strains for differentiating mutations genome-wide. To do so, genomic DNA from each of the AR strains, as well as the parent, was isolated and DNA sequencing libraries were prepared. Sequencing was performed on an Illumina MiSeq platform in a 2×300 bp paired-end configuration.

On average, 4.05 million reads per strain which equals 2,430 megabases and approximately 203-fold coverage (assuming a 12 Mb haploid genome) were obtained. The sequencing data was generally of very high quality, with 84% of Q scores greater than or equal to 30, and a mean Q score of 35.

Raw reads for each strain were trimmed and filtered for quality (Q score greater than or equal to 30) before mapping to the S288C reference genome. On average 96.12% of reads were successfully aligned. Mapped reads were used to generate pileup statistics and consensus sequences for each base in the genome. This information was then compared to the reference genome and mutations were annotated based on the S288C reference sequence. Finally, identified mutations in the AR strains were filtered against those also identified in the wild-type strain, so as to remove superfluous mutations. To increase the statistical power for identifying mutations, the RNA sequencing data originally generated for DEG were also used to call mutations. As the yeast genome is approximately 72% coding, the RNAseq data set provides good coverage for the bulk of the yeast genome.

Figure 10:
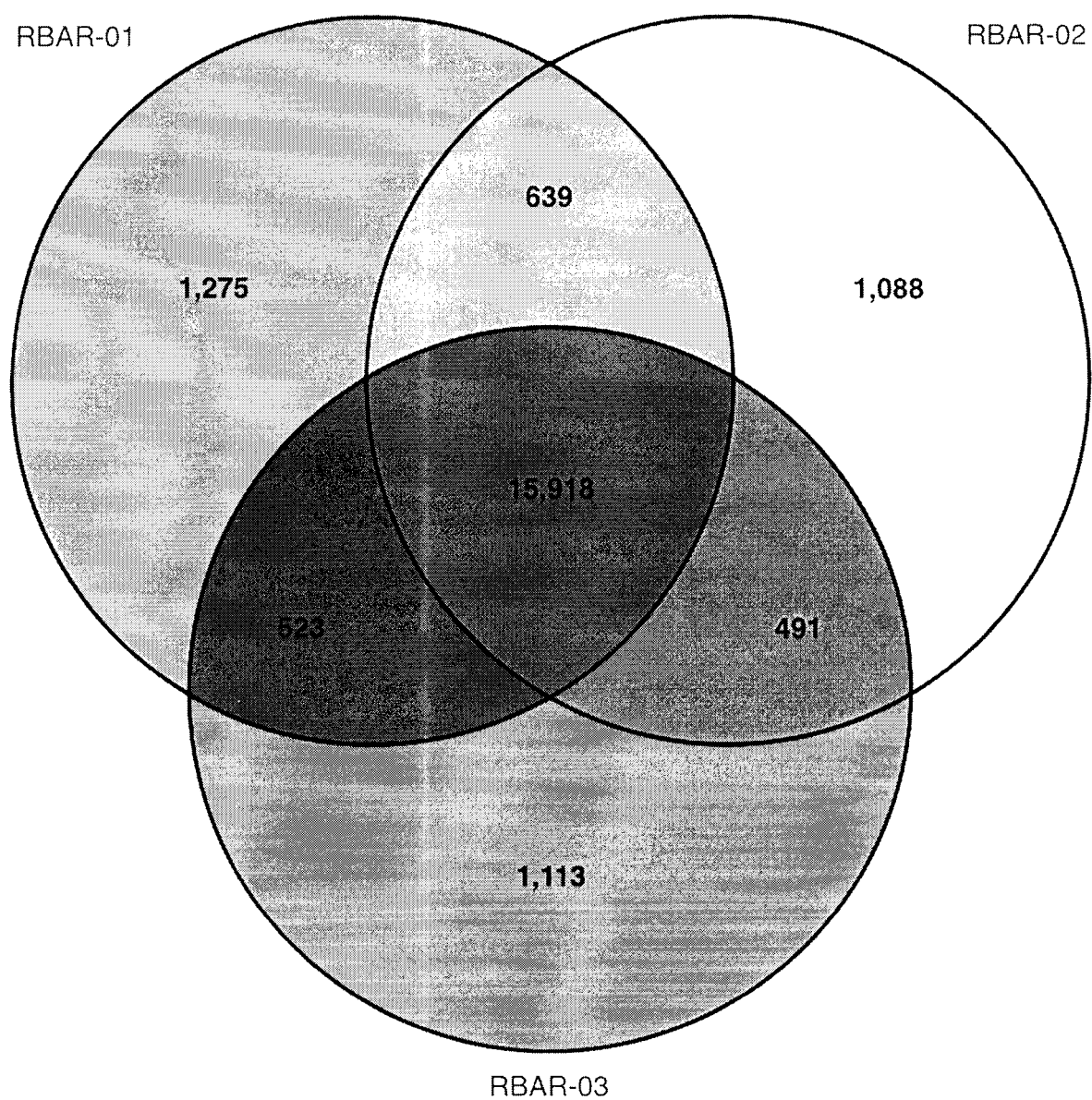
FIG. 10 shows the majority of mutations identified in the AR yeast strains are common to all. Genomic DNA was harvested from wild-type and AR yeast strains (RBAR-01, RBAR-02, and RBAR-03). DNA sequencing libraries (Nextera XT) —prepared from genomic DNA—were sequenced on an Illumina MiSeq platform in a 2×300 bp paired-end configuration. Raw reads were filtered for quality and mapped to the S288C reference genome. Read pileups were used to call variants at each nucleotide relative to the S288C consensus sequence. Variants in the AR yeast strains were filtered against wild-type variants so as to remove superfluous mutations. Venn diagram of the overlap between filtered mutations in each of the AR yeast strains.

Summary statistics for the mutational analysis are given in Tables 10 and 11. Mutational overlap comparisons between the AR strains are shown in FIG. 10. Interestingly, 15,918 out of 21,047 (75.6%) mutations were common to all three strains, while 17,571 (83.5%) were common to at least two of the AR strains (FIG. 10).

Genomic DNA was harvested from wild-type and AR yeast strains (RBAR-01, RBAR-02, and RBAR-03). DNA sequencing libraries (Nextera XT) —prepared from genomic DNA—were sequenced on an Illumina MiSeq platform in a 2×300 bp paired-end configuration. Raw reads were filtered for quality and mapped to the S288C reference genome. Read pileups were used to call variants at each nucleotide relative to the S288C consensus sequence. Variants in the AR yeast strains were filtered against wild-type variants so as to remove superfluous mutations. See Table 10.

TABLE 10

Summary of total mutations identified in DNA sequencing and RNA sequencing datasets.

| | Wild type | RBAR-01 | RBAR-02 | RBAR-03 |
|---|---|---|---|---|
| RNA sequencing | | | | |
| Identified mutations | 58,071 | 52,324 | 53,096 | 52,323 |
| Wild type filtered | — | 3,728 | 4,098 | 3,778 |
| DNA sequencing | | | | |
| Identified mutations | 58,071 | 69,567 | 69,261 | 68,979 |
| Wild type filtered | — | 17,435 | 17,190 | 17,223 |
| Combined mutations | — | 18,355 | 18,136 | 18,045 |
| RNAseq unique | — | 920 | 946 | 822 |
| DNAseq unique | — | 14,627 | 14,038 | 14,267 |
| RNA/DNA seq common | — | 2,808 | 3,152 | 2,956 |

TABLE 11

Breakdown of mutation types in AR strains. Mutations identified in Table 10 are classified according to their type.

| | RBAR-01 | RBAR-02 | RBAR-03 |
|---|---|---|---|
| Total unique mutations | 18,355 | 18,136 | 18,045 |
| Non-coding mutations | 10,820 | 10,619 | 10,690 |
| Promoter mutations[a] | 8,378 | 8,249 | 8,281 |
| TFBS[b] | 4,894 | 4,792 | 4,862 |
| Non-TFBS | 3,484 | 3,457 | 3,419 |
| Intergenic mutations | 2,442 | 2,370 | 2,409 |
| Exonic mutations | 9,205 | 9,130 | 9,028 |
| Synonymous SNV[c] | 5,630 | 5,598 | 5,540 |
| Non-synonymous SNV | 2,975 | 2,939 | 2,928 |
| Frameshift insertion | 131 | 136 | 126 |
| Frameshift deletion | 86 | 77 | 77 |
| Frameshift substitution | 21 | 16 | 12 |
| Non-frameshift insertion | 176 | 188 | 163 |
| Non-frameshift deletion | 98 | 102 | 99 |
| Non-frameshift substitution | 36 | 30 | 31 |
| Stopgain | 45 | 38 | 46 |
| Stoploss | 7 | 6 | 6 |

[a]Promoters defined by position −1000 to −1 relative to transcriptional start site
[b]Transcription factor binding site
[c]Single nucleotide variant Given that random mutagenesis and adaptive evolution are non-targeted methods, it is likely that the vast majority of mutations identified in the AR strains are superfluous to the AR phenotype i.e. constitutive expression of ASP3 and degradation of L-asparagine. Thus, the most logical place for critical mutations to occur are within the coding regions of relevant genes or else the promoters of said genes. Importantly, for coding region mutations to impact protein function, they must effect protein structure i.e. sequence. Likewise, for promoter region mutations to impact gene expression, it is likely that they should occur within transcription factor binding sites (TFBS). As such, both synonymous exonic single nucleotide variants (SNVs), as well as intergenic and non-TFBS promoter mutations can be filtered out. Taken together, these filtering criteria leaves 8,469 (4,894 TFBS and 3,575 exonic), 8,324 (4,792 TFBS and 3,532 exonic), and 8,350 (4,862 TFBS and 3,488 exonic) candidate mutations in RBAR-01, RBAR-02, and RBAR-03, respectively. Thus, it is clear that the adaptive evolution of the AR strains resulted in changes to the strains' DNA sequence, thereby allowing them to overcome NCR repression of ASP3 and constitutively degrade L-asparagine.

AR Strains Reduce Acrylamide Formation in Bread and Toast

Acrylamide forms in bread when free asparagine reacts with reducing sugars at temperatures above 120° C. Importantly, reducing sugars in bread occur in excess relative to asparagine; therefore, the levels of AA in bread are highly correlated with asparagine content (26, 67-69). Moreover, it is well established that AA levels in bread increase significantly upon toasting, when unreacted asparagine on the interior of loaves is exposed to high temperature (21). Thus, the removal of asparagine throughout the loaf prior to toasting is key to reducing the overall AA potential of bread.

Figure 11:
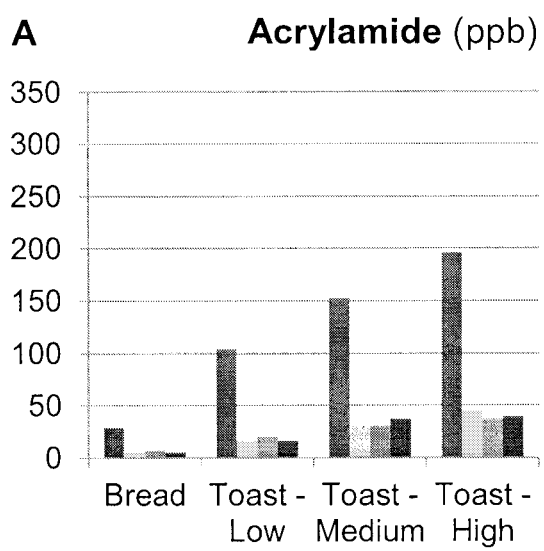
FIG. 11 shows AR yeast strains reduce acrylamide in bread and toast. White and whole wheat bread (with either 0 or 7% added sucrose) was made with either the wild-type yeast or the AR strains RBAR-01, RBAR-02, and RBAR-03. AA levels were analyzed in untoasted bread, as well as low, medium, and high toasting levels, as defined in the materials and methods. A) White bread with 0% sucrose. B) White bread with 7% sucrose. C) Whole wheat bread with 0% sucrose. D) Whole wheat bread with 7% sucrose. Data are representative of duplicate experiments.
Figure 11:
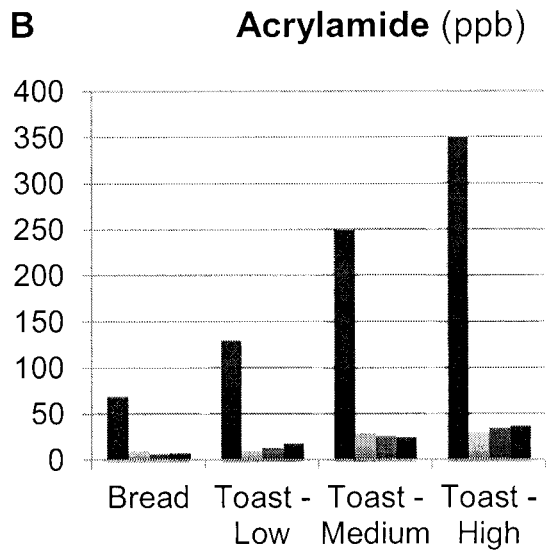
Figure 11:
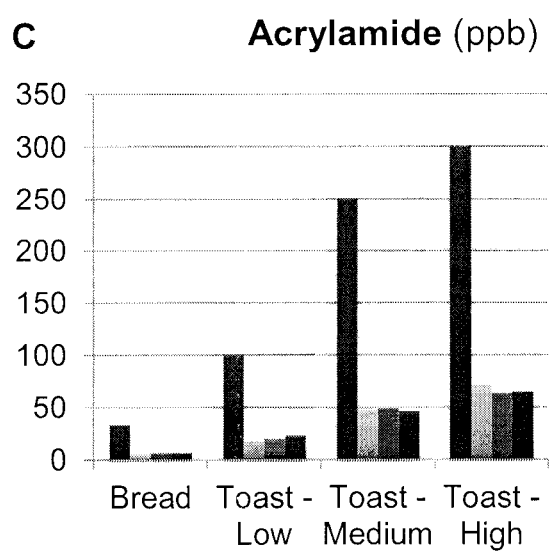
Figure 11:
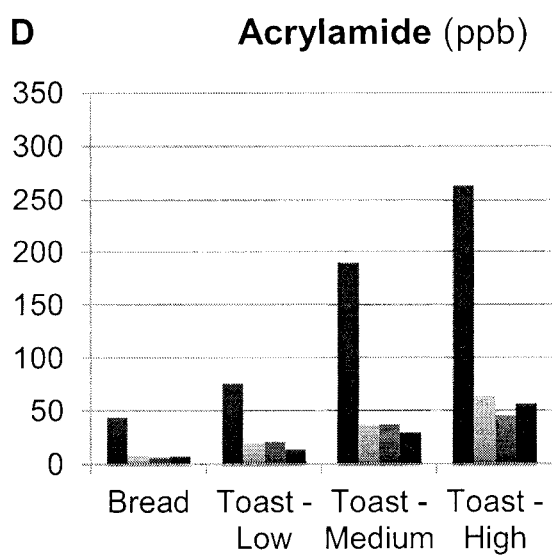

Having established that the AR yeast strains constitutively express ASP3 and degrade L-asparagine (FIGS. 2, 5, and 6), it was next wanted to determine if the strains could be used for the reduction of AA in bread. To do so, white and whole wheat bread were made with either the wild-type yeast or the AR strains RBAR-01, RBAR-02, and RBAR-03, and AA levels were analyzed in both the baked bread and toast (FIG. 11). In all breads produced with the wild-type yeast, AA levels ranged from 30-67 ppb. In contrast, all breads produced with the AR yeast strains had near undetectable levels of AA (<10 ppb), which equates to an approximate average reduction in AA of 80%. Consistent with the effects of heating on AA levels, a clear positive correlation was observed between toasting and AA levels in all breads produced by all strains. On average, low, medium and high toasting, increased AA by 3, 5, and 7 fold, respectively (FIG. 11). However, in the toast produced with the AR strains, AA levels were substantially lower, with an average reduction in AA of 75-85%. In most cases, the AA levels in toasted bread produced by the AR strains were lower than untoasted bread produced by the wild-type strain (FIG. 10). Of note, these results and conditions are representative of more than 10 independent experiments. Taken together, these results validate the AR yeast strains as a robust and seamless method for reducing AA levels in bread and toast.

AR Strains Reduce Acrylamide Formation in French Fries

As potato based foods are rich in both asparagine and reducing sugars, they tend to contain some of the highest levels of AA (12). Thus, having established that the AR yeast strains constitutively express ASP3 and degrade L-asparagine (FIGS. 2, 5, and 6), as well as their ability to substantially reduce AA levels in bread and toast (FIG. 11), it was next determined if the strains could be used for the reduction of AA in French fries. Although yeast are not an ingredient in French fries, aqueous soaking steps are common in their production. Thus, it was hypothesized that soaking potatoes in a water/yeast mixture prior to frying could reduce AA in French fries—during this time the yeast would degrade asparagine on the surface of the potato, thereby reducing AA.

Figure 12:
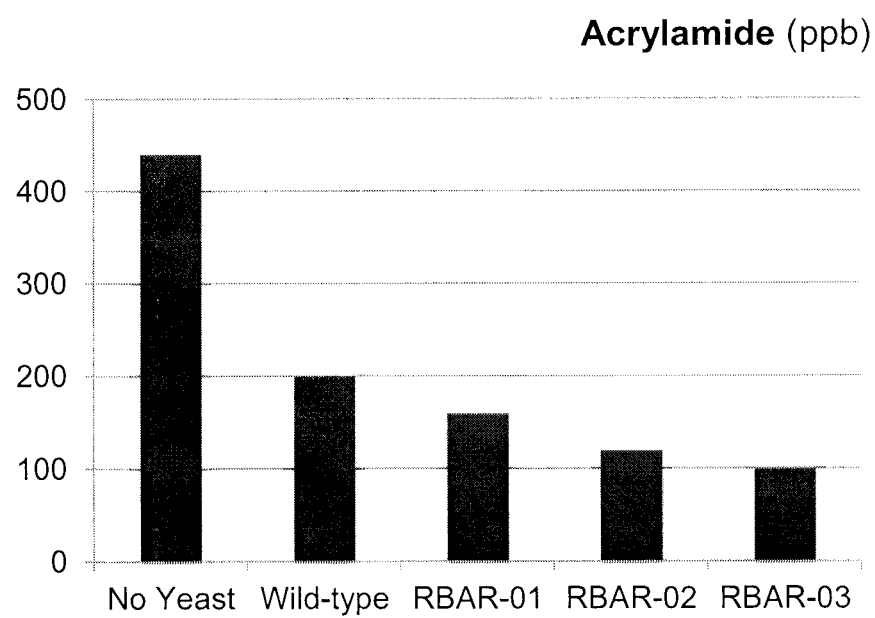
FIG. 12 shows AR yeast strains reduce acrylamide in French fries. French fries from fresh Russet potatoes were made by soaking cut, uncooked potatoes in water either without yeast, with the wild-type yeast, or with the AR strains RBAR-01, RBAR-02, and RBAR-03. AA levels were analyzed in the final fried product. Data are representative of duplicate experiments.

To test this idea, AA levels were analyzed in French fries made from fresh Russet potatoes soaked in water only, or in water/yeast solutions of either the wild-type yeast or the AR strains RBAR-01, RBAR-02, and RBAR-03 (FIG. 12). Consistent with their high sugar and asparagine content, the no yeast control French fries had high levels of AA—440 ppb. In contrast, all of the AR yeast strains were able to substantially reduce the AA content of the French fries (71% average reduction—127 ppb), with RBAR-03 yield a reduction of 77% (100 ppb). Interestingly, the wild-type yeast strain was able to reduce AA in French fries by 55% (200 ppb), relative to the no yeast control. This is likely due the natural ability of yeast to ferment sugar. Indeed, in most of the AA-affected foods i.e. non-potato based foods, asparagine is the limiting reagent for AA formation. However, in potatoes, asparagine and reducing sugars are present in roughly equimolar amounts (70) —thus, limiting reducing sugar is an effective AA mitigation measure for potatoes. However, reducing sugar and asparagine levels are known to vary depending on potato cultivar, season, and storage conditions (70). Therefore, the effectiveness of a wild-type yeast—which can only consume sugar and only under favorable processing conditions, e.g. sufficient contact time—for reducing acrylamide in potato products will be variable. As such, the AR yeast strains, with their ability to degrade asparagine, are able to significantly and consistently reduce AA levels beyond simple fermentation of sugars.

Figure 13:
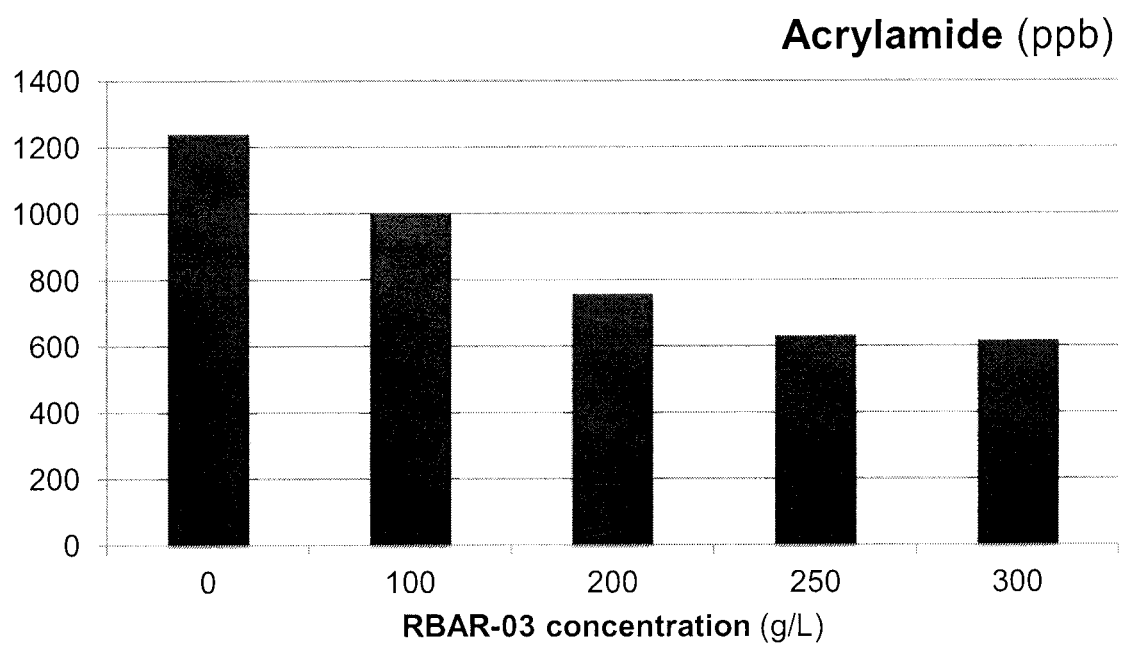
FIG. 13 shows that AR yeast strain RBAR-03 reduces acrylamide in French fries in a dose dependent manner under short incubation times and high temperature. Cut potatoes were pre-processed as described in the methods section and then incubated for 50 seconds in water alone, or water with either 100, 200, 250, or 300 g/L of AR yeast cream yeast (23% solids) at 68° C. After frying, acrylamide levels in the French fries were measured by UPLC/MS. Data are representative of triplicate experiments.

To further test the AR yeast under relatively short contact time and high temperature conditions, we prepared cut potatoes as described above and soaked them in water alone or a water/AR yeast (RBAR-03 only) mixture for 50 seconds at 68° C. As shown in FIG. 13, we observed a dose-dependent relationship between the amount of AR yeast used and the acrylamide reduction observed. Under the conditions tested, the lowest concentration of AR yeast (100 g/L) was able to reduce acrylamide by 19% (1002 ppb compared to 1240 ppb). However, at 250 g/L of AR yeast, we observed a significant reduction in acrylamide of 49% (632 ppb compared to 1240 ppb). Interestingly, we did not observe any significant benefit to using 300 g/L AR yeast, suggesting that 50% may be a maximum for acrylamide reduction under the conditions tested. However, under other more optimized conditions, acrylamide reductions by the AR yeast may be substantially higher. Of note, these results and conditions are representative of multiple independent experiments. Taken together, these data indicate that the AR yeast are effective at reducing AA in French fries, and more broadly speaking fried foods made from fresh potatoes.

AR Strains Reduce Acrylamide Formation in Snack Pellets

Figure 14:
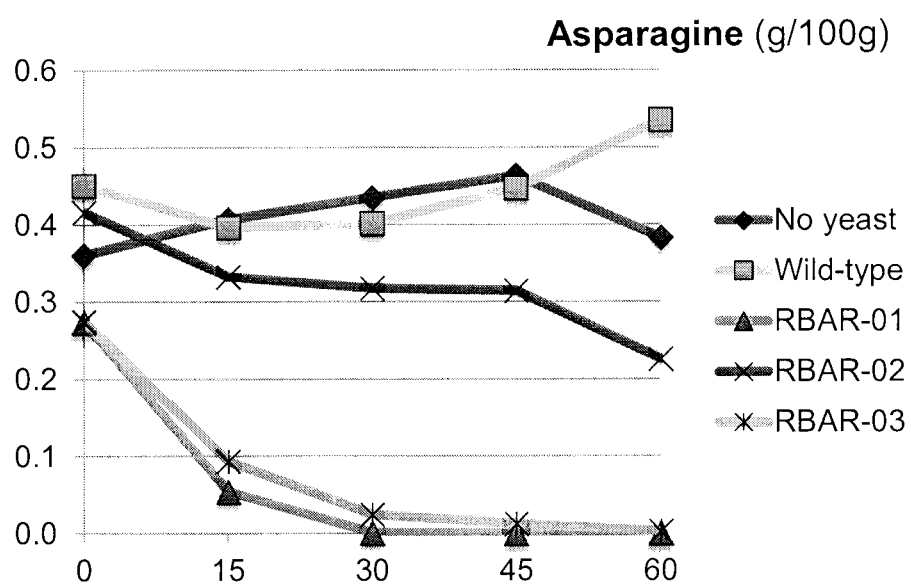
FIG. 14 shows AR yeast strains reduce acrylamide in potato based fried snacks. An extruded and fried potato based snack product was made either without yeast, with the wild-type yeast, or with the AR strains RBAR-01, RBAR-02, and RBAR-03. Asparagine levels were analyzed at various points during the production process (A) and AA levels were analyzed in the final fried product (B). Data are representative of duplicate experiments.
Figure 14:
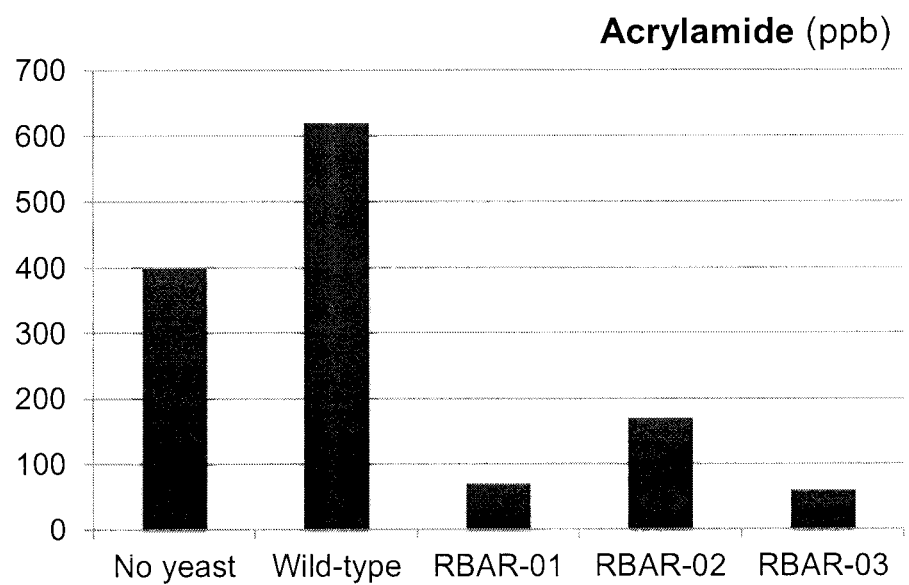

Having established the utility of the AR strains for reducing AA in fresh potato products (FIG. 14), their efficacy was next tested in potato-flour based snack foods. To do so, an extruded and fried potato based snack product were made with either the wild-type yeast or the AR strains RBAR-01, RBAR-02, and RBAR-03, and asparagine levels during processing were analyzed—AA levels were also measured in the final fried product (FIG. 14). In regards to asparagine, relative to either the no yeast control or the wild-type yeast, all of the AR strains were capable of degrading asparagine (FIG. 14A). More specifically RBAR-01 and RBAR-03 consumed all of the asparagine in the snack pellet in as little as 30 minutes treatment time. In contrast, asparagine-degradation activity in RBAR-02 was less robust in this food model-45% reduction at 60 minutes. However, this activity was easily evident, relative to the no yeast control or the wild-type yeast.

In terms of AA reduction, all of the AR strains were effective. On average, the AR strains reduced AA by 75% (100 ppb average vs. 400 ppb—FIG. 14B). Consistent with their demonstrated superior ability to degrade asparagine in this food model, RBAR-01 and RBAR-03 resulted in the lowest levels of AA-82 and 85% reduction (70 and 60 ppb), respectively (FIG. 14B). Interestingly, and contrary to the case with French fries, the wild-type yeast was not capable of reducing AA levels in the snack pellet. This is likely due to the presence of non-asparagine containing ingredients in the snack pellet mixture (potato starch and maltodextrin). These ingredients significantly increase the reducing sugar content of the mixture, thereby making asparagine the limiting reagent for AA formation in the snack pellet. As such, the sugar fermentation activity of the yeast is ineffective at reducing AA. Of note, these results and conditions are representative of multiple independent experiments. Collectively, these data confirm that the AR yeast can successfully be used to reduce AA in extruded, fried potato-flour based foods.

AR Strains Reduce Acrylamide Formation in Sweet Biscuits

Having established the utility of the AR strains for reducing AA in bread and toast, fresh potato products, and processed-potato products (FIGS. 11, 12, 13 and 14), their efficacy was next tested in sweet biscuits.

Figure 15:
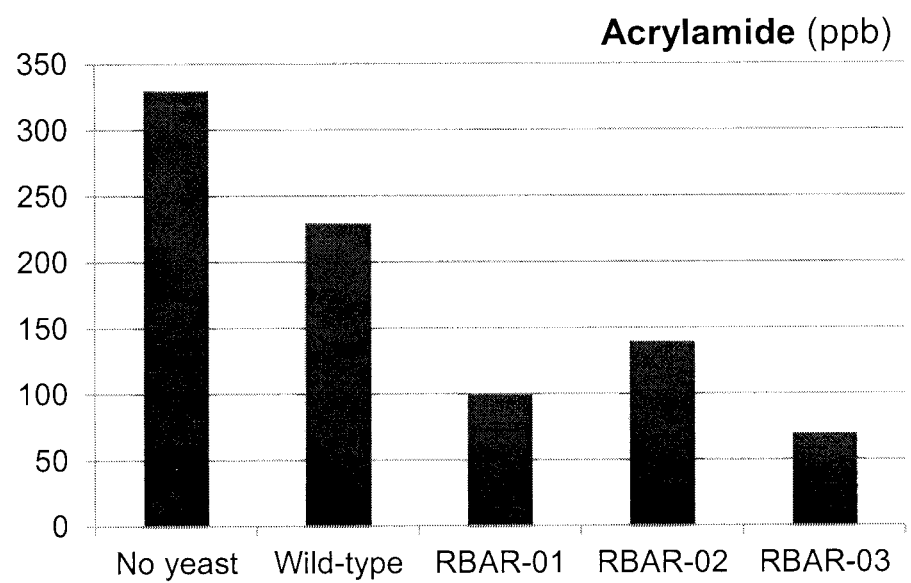
FIG. 15 shows AR yeast strains reduce acrylamide in sweet biscuits. Sweet biscuits were made either without yeast, with the wild-type yeast, or with the AR strains RBAR-01, RBAR-02, and RBAR-03. AA levels were analyzed in the final product. Data are representative of duplicate experiments.

To do so, a sweet biscuit product was made with either the wild-type yeast or the AR strains RBAR-01, RBAR-02, and RBAR-03, and analyzed AA levels in the final fried product (FIG. 15). As compared to the no yeast control, all of the AR strains were capable of reducing AA levels in the final product (average reduction 69%—average 103 ppb vs. 330 ppb), with RBAR-03 being the most effective (79% reduction—70 ppb vs. 330 ppb). Similar to the situation with the French fries (FIG. 12), it was noted that the wild-type yeast was able to reduce AA to some extent (30% reduction—230 ppb vs. 330 ppb), which is likely due to fermentative activity. However, the AR strains have greatly enhanced capacity to reduce AA due to their ability to degrade asparagine. Of note, these results and conditions are representative of multiple independent experiments. Collectively, these data indicate that the AR yeast are effective at reducing AA in sweet biscuits.

AR Strains Reduce Acrylamide Formation in Pretzels

Having established the utility of the AR strains for reducing AA in bread and toast, fresh potato products, processed-potato products, and sweet biscuits (FIGS. 11, 12, 13, 14, and 15), their efficacy was tested in pretzels. Pretzels typically contain high levels of AA due to a sodium hydroxide wash process used to increase browning during manufacturing—indeed, AA formation is accelerated at high pH.

Figure 16:
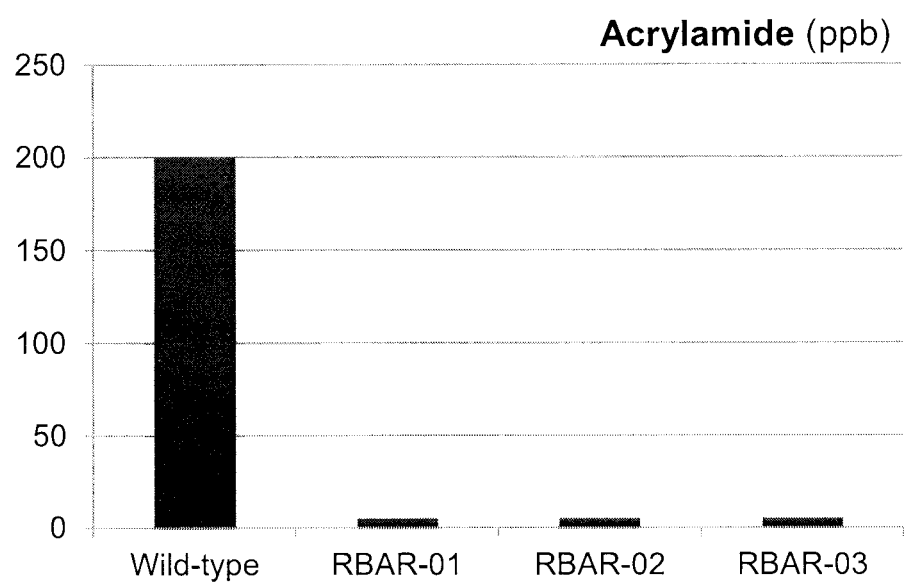
FIG. 16 shows AR yeast strains reduce acrylamide in pretzels. Pretzels were made either with the wild-type yeast, or with the AR strains RBAR-01, RBAR-02, and RBAR-03. AA levels were analyzed in the final product. Data are representative of duplicate experiments.

Pretzels were made with either the wild-type yeast or the AR strains RBAR-01, RBAR-02, and RBAR-03, and AA levels analyzed in the final product (FIG. 16). Compared to the wild-type yeast, all of the AR strains were extremely capable of reducing AA levels in the final product (average reduction 98%—average<5 ppb vs. 200 ppb). Of note, these results and conditions are representative of multiple independent experiments. Collectively, these data indicate that the AR yeast are highly effective at reducing AA in pretzels.

AR Yeast Reduce Asparagine and Acrylamide Formation in Coffee

Figure 17:
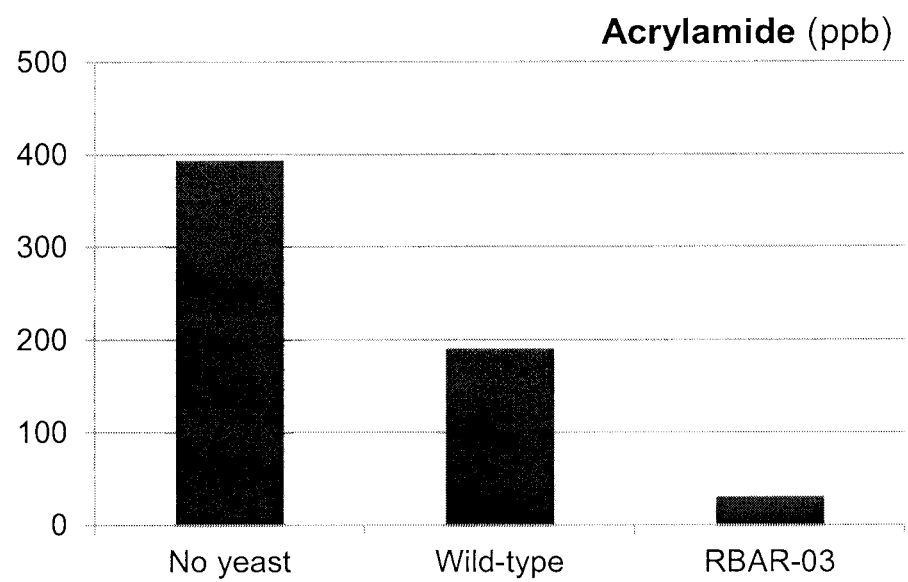
FIG. 17 shows AR yeast strains reduce acrylamide in coffee through direct fermentation of green coffee beans. Ground green coffee beans were incubated in either water alone, the wild-type yeast, or the AR strain RBAR-03. After incubation, ground beans were dried and roasted, after which AA levels were analyzed.

Having established the utility of the AR strains for reducing AA in bread and toast, fresh potato products, processed-potato products, sweet biscuits, and pretzels (FIGS. 11, 12, 13, 14, 15, and 16), their efficacy was tested in coffee. As a first proof-of-concept, the wild-type and AR yeast strain RBAR-03 was tested in fermentations of ground green coffee beans (FIG. 17). Compared to the no yeast control, the wild-type strain reduced AA by 52% (191 ppb vs. 394 ppb), presumably due to fermentation of reducing sugars in the bean. However, the AR strain RBAR-03, with its ability to consume both sugar and asparagine, reduced AA by 92% (32 ppb vs. 394 ppb).

Given that the AR yeast is able to reduce AA when applied directly to ground green coffee beans (FIG. 17), the ability of the AR yeast to reduce asparagine was next tested in an aqueous green coffee extract. Such extracts, when depleted for compounds of interest, e.g. asparagine or caffeine, can then be used to selectively remove that compound from green coffee beans prior to roasting. If asparagine is removed in this way, AA will be lowered in the resultant roasted coffee.

Figure 18:
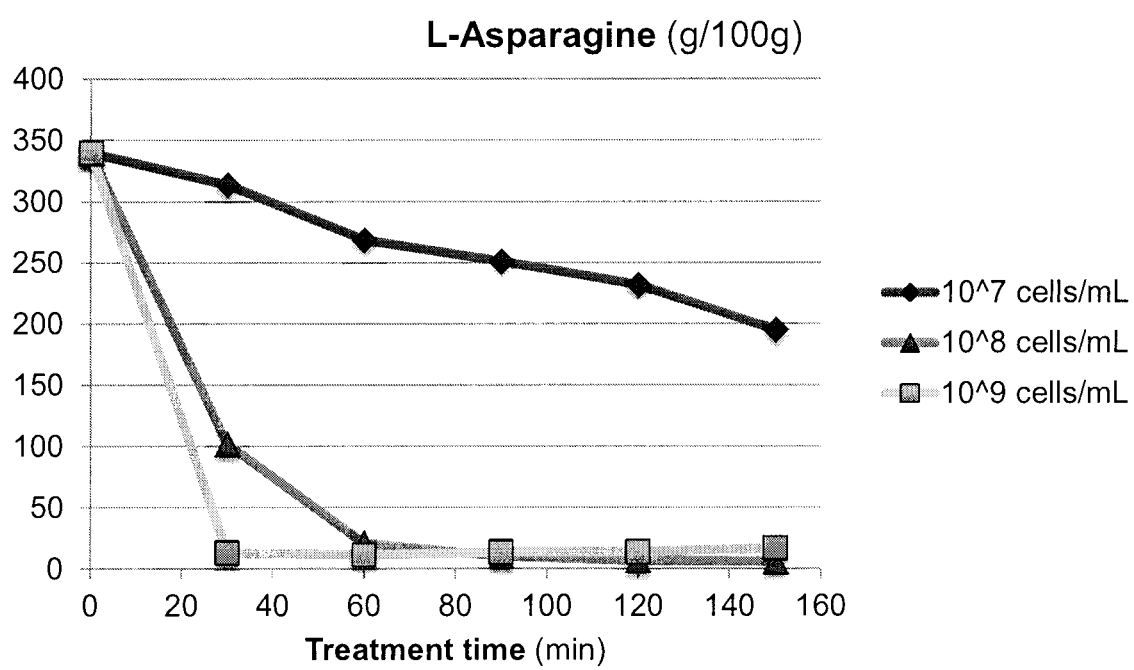
FIG. 18 shows AR yeast strains reduce asparagine in green coffee extract. Green coffee extract (18% soluble solids) were incubated with AR yeast at various concentrations. After incubation, extracts were clarified by centrifugation and L-Asparagine levels were analyzed. Data are representative of duplicate experiments.

As shown in FIG. 18, the AR yeast (RBAR-03) is capable of reducing L-Asparagine in GCE (18% solids) in a time and concentration dependent manner. At the highest concentration of AR yeast ($10^9$ cells/mL), greater than 95% of the L-Asparagine was consumed within 30 minutes (340 g/100 g L-Asparagine, time=0 vs. 13.1 g/100 g L-Asparagine, time=30 min), while at the intermediate concentration ($10^8$ cells/mL), this was achieved within 90 minutes (340 g/100 g L-Asparagine, time=0 vs. 10.5 g/100 g L-Asparagine, time=30 min). At the lowest concentration of AR yeast ($10^7$ cells/mL), L-Asparagine consumption was incomplete, with only 43% reduction at 150 minutes (340 g/100 g L-Asparagine, time=0 vs. 195 g/100 g L-Asparagine, time=150 min). Of note, these results and conditions are representative of multiple independent experiments. Taken together, these data confirm that the AR strains—which have the ability to degrade L-Asparagine—are capable of efficiently reducing L-Asparagine and AA in coffee.

CONCLUSION

Despite the obvious need for better AA reduction tools, currently available methods either do not offer high enough efficacy, or are technically, logistically, and financially difficult to implement. To address these issues, a novel AA reduction technology based on baker's yeast was developed. Using yeast to drive AA reduction in food is an ideal solution because 1) it is already a natural food ingredient to which humans have a long history of exposure; 2) yeast is subject to US FDA 'Generally Regarded As Safe' (GRAS) status or international equivalents in most jurisdictions worldwide; 3) yeast is already a major ingredient in many of the foods for which AA is a significant problem e.g. bread; 4) AR yeast can be incorporated as a transient treatment to other foods for which AA is an issue e.g. potato products, cereals, snack foods and coffee; 5) yeast are inexpensive to grow and easy to work with and 6) most commercial food producers have pre-existing experience working with yeast. Moreover, being adaptively evolved from a baker's yeast strain, the AR yeast strains can seamlessly and easily replace baker's yeast in all existing baking processes as no changes in industrial baking processes are required in order to use the AR yeast, be it for the production of bread or any yeast-fermented baked product.

As described in this report, the non-genetically modified, adaptively evolved AR baker's yeast strains—which constitutively express the cell wall-associated Asparaginase 11 ASP3 (FIGS. 2, 5, and 6) —are a robust and highly efficacious solution to the AA problem in food. The AR yeast strains are capable of substantially reducing asparagine levels in a variety of foods by up to 95% with minimal exposure time and processing change (FIGS. 11, 12, 13, 14, 15, 16, 17, and 18) —in foods where yeast is already an ingredient, no processing change is required.

By substantially degrading asparagine in food products prior to cooking, the technology prevents the formation of AA irrespective of downstream food handling practices i.e. AR strains reduce the AA potential of foods. This circumvents the need for a multi-pronged AA control and reduction strategy—involving a vast range of parameters and representing broad scale intervention—that is logistically and technically challenging to implement, extremely costly, and difficult to regulate (e.g. home and restaurant food preparation).

In summary, adaptive evolution was used to develop novel, non-GMO baker's yeast strains that constitutively express the cell-wall associated Asparaginase II (ASPS) and degrade L-asparagine to reduce AA levels in a wide variety of common food items. The AR strains are capable of reducing AA levels in bread and other yeast-fermented foods, potato based foods, extruded snack foods, sweet biscuits, pretzels, and coffee by up to 95%.

While the present disclosure has been described with reference to what are presently considered to be the examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Besaratinia A, Pfeifer G P. 2007. A review of mechanisms of acrylamide carcinogenicity. Carcinogenesis 28:519-528.
2. Exon J H. 2006. A Review of the Toxicology of Acrylamide. Journal of Toxicology and Environmental Health, Part B 9:397-412.
3. Capuano E, Fogliano V. 2011. Acrylamide and 5-hydroxymethylfurfural (HMF): A review on metabolism, toxicity, occurrence in food and mitigation strategies. LWT—Food Science and Technology 44:793-810.
4. Shipp A, Lawrence G, Gentry R, McDonald T, Bartow H, Bounds J, Macdonald N, Clewell H, Allen B, Van Landingham C. 2006. Acrylamide: review of toxicity data and dose-response analyses for cancer and noncancer effects. Crit. Rev. Toxicol. 36:481-608.
5. Besaratinia A, Pfeifer G P. 2004. Genotoxicity of acrylamide and glycidamide. J. Natl. Cancer Inst 96:1023-1029.
6. Rice J M. 2005. The carcinogenicity of acrylamide. Mutation Research/Genetic Toxicology and Environmental Mutagenesis 580:3-20.
7. Mottram D S, Wedzicha B L, Dodson A T. 2002. Acrylamide is formed in the Maillard reaction. Nature 419: 448-449.
8. Stadler R H, Blank I, Varga N, Robert F, Hau J, Guy P A. 2002. Food chemistry: acrylamide from Maillard reaction products. Nature 419:449-450.
9. Tareke E, Rydberg P, Karlsson P, Eriksson S, Törnqvist M. 2002. Analysis of Acrylamide, a Carcinogen Formed in Heated Foodstuffs. Journal of Agricultural and Food Chemistry 50:4998-5006.
10. Normandin L, Bouchard M, Ayotte P, Blanchet C, Becalski A, Bonvalot Y, Phaneuf D, Lapointe C, Gagné M, Courteau M. 2013. Dietary exposure to acrylamide in adolescents from a Canadian urban center. Food and Chemical Toxicology 57:75-83.
11. Chen Y-H, Xia E-Q, Xu X-R, Ling W-H, Li S, Wu S, Deng G-F, Zou Z-F, Zhou J, Li H-B. 2012. Evaluation of Acrylamide in Food from China by a LC/MS/MS Method. IJERPH 9:4150-4158.
12. Wenzl T, Anklam E. 2007. European Union database of acrylamide levels in food: Update and critical review of data collection. Food Additives and Contaminants 24:5-12.
13. Mojska H, Gielecińska I, Szponar L, Ottarzewski M. 2010. Estimation of the dietary acrylamide exposure of the Polish population. Food and Chemical Toxicology 48:2090-2096.
14. Tran N L, Barraj L M, Murphy M M, Bi X. 2010. Dietary Acrylamide Exposure and Hemoglobin Adducts — National Health and Nutrition Examination Survey (2003–04). Food and Chemical Toxicology 48:3098-3108.
15. Sirot V R, Hommet F, Tard A, Leblanc J-C. 2012. Dietary acrylamide exposure of the French population: Results of the second French Total Diet Study. Food and Chemical Toxicology 50:889-894.
16. Zhou P P, Zhao Y F, Liu H L, Ma Y J, Li X W, Yang X, Wu Y N. 2013. Dietary exposure of the Chinese population to acrylamide. Biomed. Environ. Sci. 26:421-429.
17. Mojska H, Gielecińska I, Stoś K. 2012. Determination of acrylamide level in commercial baby foods and an assessment of infant dietary exposure. Food and Chemical Toxicology 50:2722-2728.
18. Cengiz M F, Gündüz C P B. 2013. Acrylamide exposure among Turkish toddlers from selected cereal-based baby food samples. Food and Chemical Toxicology 60:514-519.
19. Bent G-A, Maragh P, Dasgupta T. 2012. Acrylamide in Caribbean foods — Residual levels and their relation to reducing sugar and asparagine content. Food Chemistry 133:451-457.
20. Pelucchi C, Bosetti C, Galeone C, La Vecchia C. 2014. Dietary acrylamide and cancer risk: An updated meta-analysis. Int. J. Cancer 136:2912-2922.
21. Jackson L S, Al-Taher F. 2005. Effects of consumer food preparation on acrylamide formation. Advances in Experimental Medicine and Biology 561:447-465.
22. Fredriksson H, Tallying J, Rosén J, Åman P. 2004. Fermentation reduces free asparagine in dough and acrylamide content in bread. Cereal Chemistry 81:650-653.
23. Bråthen E, Kite A, Knutsen S H, Wicklund T. 2005. Addition of Glycine Reduces the Content of Acrylamide in Cereal and Potato Products. Journal of Agricultural and Food Chemistry 53:3259-3264.
24. Fink M, Andersson R, Rosén J, Åman P. 2006. Effect of Added Asparagine and Glycine on Acrylamide Content in Yeast-Leavened Bread. Cereal Chemistry 83:218-222.
25. Gökmen V, Palazoğlu T K. 2007. Acrylamide Formation in Foods during Thermal Processing with a Focus on Frying. Food Bioprocess Technol 1:35-42.
26. Amrein T M, Schönbächler B, Escher F, Amadó R. 2004. Acrylamide in Gingerbread: Critical Factors for Formation and Possible Ways for Reduction. Journal of Agricultural and Food Chemistry 52:4282-4288.
27. Claus A, Schreiter P, Weber A, Graeff S, Herrmann W, Claupein W, Schieber A, Carle R. 2006. Influence of Agronomic Factors and Extraction Rate on the Acrylamide Contents in Yeast-Leavened Breads. Journal of Agricultural and Food Chemistry 54:8968-8976.
28. Claus A, Mongili M, Weisz G, Schieber A, Carle R. 2008. Impact of formulation and technological factors on the acrylamide content of wheat bread and bread rolls. Journal of Cereal Science 47:546-554.
29. Chawla R, Shakya R, Rommens C M. 2012. Tuber-specific silencing of asparagine synthetase-1 reduces the acrylamide-forming potential of potatoes grown in the field without affecting tuber shape and yield. Plant Biotechnology Journal 10:913-924.
30. Ye J, Shakya R, Shrestha P, Rommens C M. 2010. Tuber-Specific Silencing of the Acid Invertase Gene Substantially Lowers the Acrylamide-Forming Potential of Potato. Journal of Agricultural and Food Chemistry 58:12162-12167.
31. Rommens C M, Yan H, Swords K, Richael C, Ye J. 2008. Low-acrylamide French fries and potato chips. Plant Biotechnology Journal 6:843-853.
32. Cooper T G. 1982. Nitrogen metabolism in *S. cerevisiae*, pp. 39-99. In J. N. Strathern, E W J (ed.), The molecular biology of the yeast: metabolism and gene expression. Cold Spring Harbor Press, New York.
33. Jones G E. 1977. Genetic and physiological relationships between L-asparaginase I and asparaginase II in *Saccharomyces cerevisiae*. Journal of Bacteriology 130:128-130.
34. League G P, Slot J C, Rokas A. 2012. The ASP3 locus in *Saccharomyces cerevisiae* originated by horizontal gene transfer from *Wickerhamomyces*. FEMS Yeast Research 12:859-863.
35. Sinclair K, Warner J P, Bonthron D T. 1994. The ASP1 gene of *Saccharomyces cerevisiae*, encoding the intracellular isozyme of L-asparaginase. Gene 144:37-43.
36. Kim K W, Kamerud J Q, Livingston D M, Roon R J. 1988. Asparaginase II of *Saccharomyces cerevisiae*. Characterization of the ASP3 gene. Journal of Biological Chemistry 263:11948-11953.
37. Dunlop P C, Meyer G M, Roon R J. 1980. Nitrogen catabolite repression of asparaginase II in *Saccharomyces cerevisiae*. Journal of Bacteriology 143:422-426.
38. Huang Y-C, Chen H-T, Teng S-C. 2010. Intragenic transcription of a noncoding RNA modulates expression of ASP3 in budding yeast. RNA (New York, N.Y.) 16:2085-2093.

39. Pauling K D, Jones G E. 1980. Asparaginase II of *Saccharomyces cerevisiae*: Dynamics of Accumulation and Loss in Rapidly Growing Cells. J. Gen. Microbiol. 117:423-430.
40. Roon R J, Murdoch M, Kunze B, Dunlop P C. 1982. Derepression of asparaginase II during exponential growth of *Saccharomyces cerevisiae* on ammonium ion. Arch. Biochem. Biophys. 219:101-109.
41. Ferrara M A, Mattoso J M V, Bon E P S, Pereira N. 2004. Kinetics of asparaginase II fermentation in *Saccharomyces cerevisiae* ure2dal80 mutant: effect of nitrogen nutrition and pH. Applied Biochemistry and Biotechnology 113-116:299-305.
42. Hofman-Bang J. 1999. Nitrogen catabolite repression in *Saccharomyces cerevisiae*. Molecular biotechnology 12:35-73.
43. Derkx P M, Janzen T, Sørensen K I, Christensen J E, Stuer-Lauridsen B, Johansen E. 2014. The art of strain improvement of industrial lactic acid bacteria without the use of recombinant DNA technology. Microb. Cell Fact. 13:S5.
44. Pedersen M B, Iversen S L, Sørensen K I, Johansen E. 2005. The long and winding road from the research laboratory to industrial applications of lactic acid bacteria. FEMS microbiology reviews 29:611-624.
45. Margolies A, Sanchez B. 2012. Selection of a *Bifidobacterium animalis* subsp. *lactis* Strain with a Decreased Ability To Produce Acetic Acid. Applied and Environmental Microbiology 78:3338-3342.
46. Saarela M, Alakomi H L, Mättö J, Ahonen A M, Puhakka A, Tynkkynen S. 2011. Improving the storage stability of *Bifidobacterium breve* in low pH fruit juice. International Journal of Food Microbiology 149:106-110.
47. Smith J, van Rensburg E, Görgens J F. 2014. Simultaneously improving xylose fermentation and tolerance to lignocellulosic inhibitors through evolutionary engineering of recombinant *Saccharomyces cerevisiae* harbouring xylose isomerase. BMC Biotechnol. 14:41.
48. Bachmann H, Starrenburg M J C, Molenaar D, Kleerebezem M, van Hylckama Vlieg J E T. 2012. Microbial domestication signatures of *Lactococcus lactis* can be reproduced by experimental evolution. Genome research 22:115-124.
49. guez J O V-R, Shi S, Siewers V, Nielsen J. 2014. Metabolic engineering of *Saccharomyces cerevisiae* for production of fatty acid ethyl esters, an advanced biofuel, by eliminating non-essential fatty acid utilization pathways. APPLIED ENERGY 115:226-232.
50. Callanan M J, Beresford T P, Ross R P. 2005. Genetic Diversity in the Lactose Operons of *Lactobacillus helveticus* Strains and Its Relationship to the Role of These Strains as Commercial Starter Cultures. Applied and Environmental Microbiology 71:1655-1658.
51. Çakar Z P, B, Alkim C, Yilmaz Ü. 2011. Evolutionary engineering of *Saccharomyces cerevisiae* for improved industrially important properties. FEMS Yeast Res 12:171-182.
52. Winkler J D, Kao K C. 2014. Recent advances in the evolutionary engineering of industrial biocatalysts. Genomics 104:406-411.
53. Stanley D, Fraser S, Chambers P J, Rogers P, Stanley G A. 2009. Generation and characterisation of stable ethanol-tolerant mutants of *Saccharomyces cerevisiae*. Journal of Industrial Microbiology and Biotechnology 37:139-149.
54. Liu E, Hu Y. 2010. Construction of a xylose-fermenting *Saccharomyces cerevisiae* strain by combined approaches of genetic engineering, chemical mutagenesis and evolutionary adaptation. Biochemical Engineering Journal 48:204-210.
55. Stroman P, Muller C C, Sorensen K I. 2003. Heat Shock Treatment Increases the Frequency of Loss of an Erythromycin Resistance-Encoding Transposable Element from the Chromosome of *Lactobacillus* crispatus CHCC3692. Applied and Environmental Microbiology 69:7173-7180.
56. Dragosits M, Mattanovich D. 2013. Adaptive laboratory evolution ☐ principles and applications for biotechnology. Microb. Cell Fact. 12:1-1.
57. Gresham D, Usaite R, Germann S M, Lisby M, Botstein D, Regenberg B. 2010. Adaptation to diverse nitrogen-limited environments by deletion or extrachromosomal element formation of the GAP1 locus. Proceedings of the National Academy of Sciences of the United States of America 107:18551-18556.
58. Hong J, Gresham D. 2014. Molecular Specificity, Convergence and Constraint Shape Adaptive Evolution in Nutrient-Poor Environments. PLoS genetics 10:e1004041-16.
59. WATANABE T, IEFUJI H, KITAMOTO H K. 2013. Genome-wide screening to study breeding methods to improve the nitrogen accumulation ability of yeast without gene recombinant techniques. Bioscience, biotechnology, and biochemistry 77:917-922.
60. Kamerud J Q, Roon R J. 1986. Asparaginase II of *Saccharomyces cerevisiae*: selection of four mutations that cause derepressed enzyme synthesis. Journal of Bacteriology 165:293-296.
61. Tristezza M, Gerardi C, Logrieco A, Grieco F. 2009. An optimized protocol for the production of interdelta markers in *Saccharomyces cerevisiae* by using capillary electrophoresis. Journal of Microbiological Methods 78:286-291.
62. Hoffman C S, Winston F. 1987. A ten-minute DNA preparation from yeast efficiently releases autonomous plasmids for transformation of *Escherichia coli*. Gene 57:267-272.
63. Köhrer K, Domdey H. 1991. Preparation of high molecular weight RNA. Methods in enzymology 194: 398-405.
64. Dunlop P C, Roon R J, Even H L. 1976. Utilization of D-asparagine by *Saccharomyces cerevisiae*. Journal of Bacteriology 125:999-1004.
65. Roon R J, Even H L, Dunlop P, Larimore F L. 1975. Methylamine and ammonia transport in *Saccharomyces cerevisiae*. Journal of Bacteriology 122:502-509.
66. Roon R J, Levy J S, Larimore F. 1977. Negative interactions between amino acid and methylamine/ammonia transport systems of *Saccharomyces cerevisiae*. Journal of Biological Chemistry 252:3599-3604.
67. Keramat J, LeBail A, Prost C, Jafari M. 2010. Acrylamide in Baking Products: A Review Article. Food Bioprocess Technol 4:530-543.
68. Capuano E, Ferrigno A, Acampa I, Serpen A, Açar Ö Ç, Gökmen V, Fogliano V. 2009. Effect of flour type on Maillard reaction and acrylamide formation during toasting of bread crisp model systems and mitigation strategies. FRIN 42:1295-1302.
69. Surdyk N, Rosen J, Andersson R, Åman P. 2004. Effects of Asparagine, Fructose, and Baking Conditions on Acrylamide Content in Yeast-Leavened Wheat Bread. Journal of Agricultural and Food Chemistry 52:2047-2051.
70. Halford N G, Curtis T Y, Muttucumaru N, Postles J, Elmore J S, Mottram D S. 2012. The acrylamide problem: a plant and agronomic science issue. Journal of Experimental Botany 63:2841-2851.
71. Ljungdahl P O, Daignan-Fornier B. 2012. Regulation of amino acid, nucleotide, and phosphate metabolism in *Saccharomyces cerevisiae*. Genetics 190:885-929.

The invention claimed is:

1. An isolated industrial yeast that degrades L-asparagine under non-inducing conditions produced by a method comprising:
   a) subculturing a wild-type industrial yeast strain, which expresses or has the capacity to express a cell-wall associated Asparaginase, in the presence of media containing D-asparagine as the sole nitrogen source;
   b) continuously subculturing, tracking growth rate and subjecting to mutagenesis weekly to produce cells that have multiple random mutations compared to the cells prior to subculturing;
   c) selecting cultures of b) when the growth rate reaches baseline;
   d) continuously subculturing cells in selective media containing methylamine, tracking growth rate, and mutagenizing weekly until growth rate in the presence of methylamine reaches that in selective media without methylamine to enrich for cells that have relevant multiple random mutations compared to the cells prior to subculturing in the selective media containing methylamine;
   e) isolating individual colonies of d) by plating on selective media containing methylamine, growing said colonies and selecting large and fast growing colonies;
   f) assaying selected colonies of e) for the ability to degrade L-asparagine under non-inducing conditions and selecting at least one colony with high L-asparagine degradation activity, as compared to cells at the start of d);
   g) repeating steps d) through f), increasing methylamine concentration each time, until L-asparagine degradation activity reaches a plateau;
   h) isolating the strain from g) in which L-asparagine degradation activity has reached a plateau.

2. The isolated industrial yeast strain of claim 1 wherein the industrial yeast possess greater than 18,000 unique genetic mutations.

3. An isolated industrial yeast strain deposited with the International Depositary Authority of Canada (IDAC) under accession number 140515-01 (RBAR-01) wherein the yeast degrades L-asparagine under non-inducing conditions.

4. An isolated industrial yeast strain deposited with the International Depositary Authority of Canada (IDAC) under accession number 140515-02 (RBAR-02); wherein the yeast degrades L-asparagine under non-inducing conditions.

5. An isolated industrial yeast strain deposited with the International Depositary Authority of Canada (IDAC) under accession number 140515-03 (RBAR-03); wherein the yeast degrades L-asparagine under non-inducing conditions.

6. A food product having a reduced asparagine or acrylamide concentration comprising the industrial yeast strain of claim 3.

7. A food product having a reduced asparagine or acrylamide concentration comprising the industrial yeast strain of claim 4.

8. A food product having a reduced asparagine or acrylamide concentration comprising the industrial yeast strain of claim 5.

* * * * *